(12) United States Patent
Ikehara

(10) Patent No.: US 11,439,468 B2
(45) Date of Patent: Sep. 13, 2022

(54) FLUORESCENT IMAGING DEVICE

(71) Applicant: SHIMADZU CORPORATION, Kyoto (JP)

(72) Inventor: Tatsuya Ikehara, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 889 days.

(21) Appl. No.: 16/270,758

(22) Filed: Feb. 8, 2019

(65) Prior Publication Data
US 2019/0247126 A1  Aug. 15, 2019

(30) Foreign Application Priority Data
Feb. 9, 2018 (JP) .............................. JP2018-021597

(51) Int. Cl.
*A61B 34/20* (2016.01)
*A61B 5/00* (2006.01)
*A61B 5/11* (2006.01)
*A61B 5/1455* (2006.01)
*G06T 7/246* (2017.01)
(Continued)

(52) U.S. Cl.
CPC .......... *A61B 34/20* (2016.02); *A61B 1/00045* (2013.01); *A61B 1/00096* (2013.01); *A61B 1/043* (2013.01); *A61B 1/0638* (2013.01); *A61B 1/0653* (2013.01); *A61B 5/0071* (2013.01); *A61B 5/1128* (2013.01); *A61B 5/14556* (2013.01); *A61B 5/7425* (2013.01); *G06T 7/248* (2017.01); *A61B 5/0033* (2013.01); *A61B 2034/2057* (2016.02); *G06T 2207/10048* (2013.01); *G06T 2207/10064* (2013.01);
(Continued)

(58) Field of Classification Search
CPC . A61B 34/20; A61B 1/00045; A61B 1/00096; A61B 1/043; A61B 1/0638; A61B 1/0653; A61B 5/0071; A61B 5/1128; A61B 5/14556; A61B 5/7425; A61B 5/0033; A61B 2034/2057; G06T 7/248; G06T 2207/10048; G06T 2207/10064; G06T 2207/30048; G06T 2207/30104
See application file for complete search history.

(56) References Cited

U.S. PATENT DOCUMENTS 6,582,370 B2  6/2003  Jibiki
7,756,562 B2  7/2010  Kimura
(Continued)

FOREIGN PATENT DOCUMENTS

JP  3495710 B2  2/2004
JP  4537681 B2  9/2010
JP  4745059 B2  8/2011

OTHER PUBLICATIONS

Communication dated Apr. 10, 2019 from the European Patent Office in application No. 19155416.1.

*Primary Examiner* — Peter Luong
(74) *Attorney, Agent, or Firm* — Sughrue Mion, PLLC

(57) ABSTRACT

A fluorescent imaging device includes a light source unit including a first light source for radiating excitation light, a second light source for radiating visible illumination light, and a third light source for radiating non-visible light, an imager being configured to capture a fluorescent image, a visible image, and a non-visible image, and a tracking processor that is operable to perform moving-body tracking for a region of interest that is set in an image based on at least the non-visible image.

15 Claims, 11 Drawing Sheets

(51) Int. Cl.
  *A61B 1/00*     (2006.01)
  *A61B 1/04*     (2006.01)
  *A61B 1/06*     (2006.01)

(52) U.S. Cl.
  CPC .............. *G06T 2207/30048* (2013.01); *G06T 2207/30104* (2013.01)

(56) References Cited

U.S. PATENT DOCUMENTS

| | | |
|---|---|---|
| 8,190,231 B2 | 5/2012 | Miwa et al. |
| 2006/0247535 A1 | 11/2006 | Sendai |
| 2016/0287081 A1 | 10/2016 | Yang et al. |
| 2017/0004344 A1* | 1/2017 | Nozato ................ A61B 3/1025 |

* cited by examiner

FIRST EMBODIMENT

FIRST EMBODIMENT

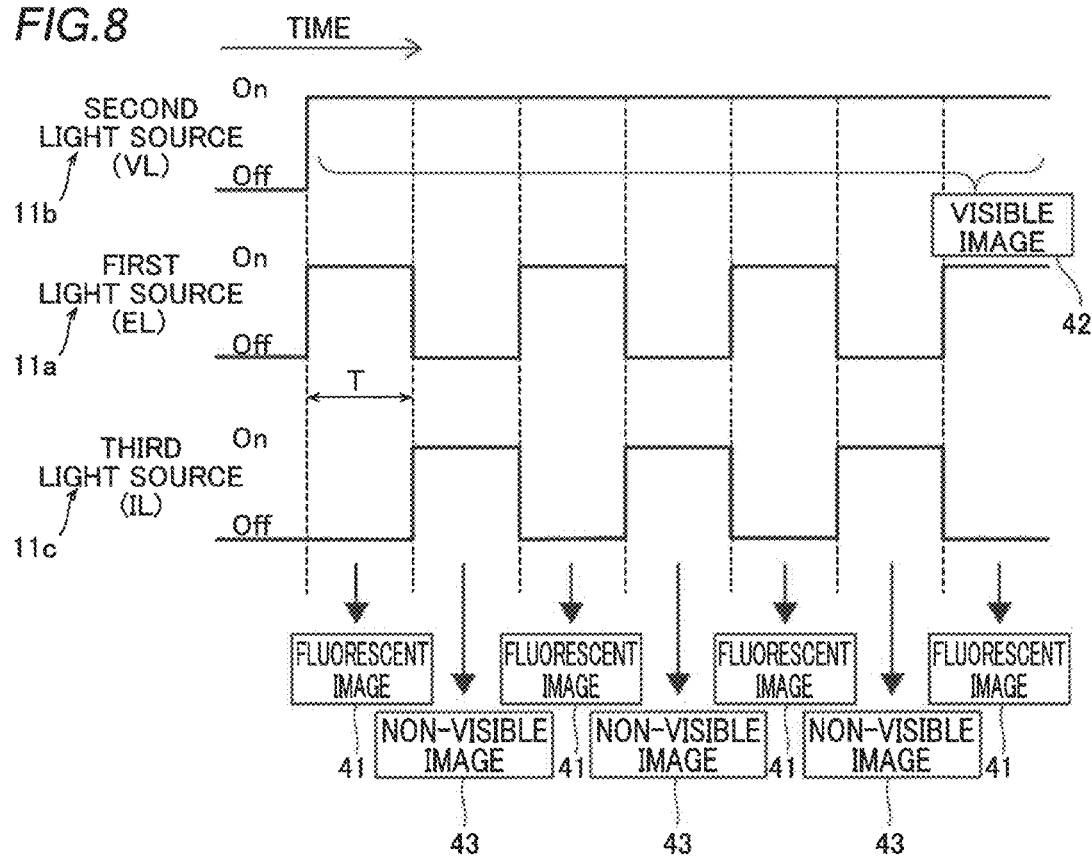
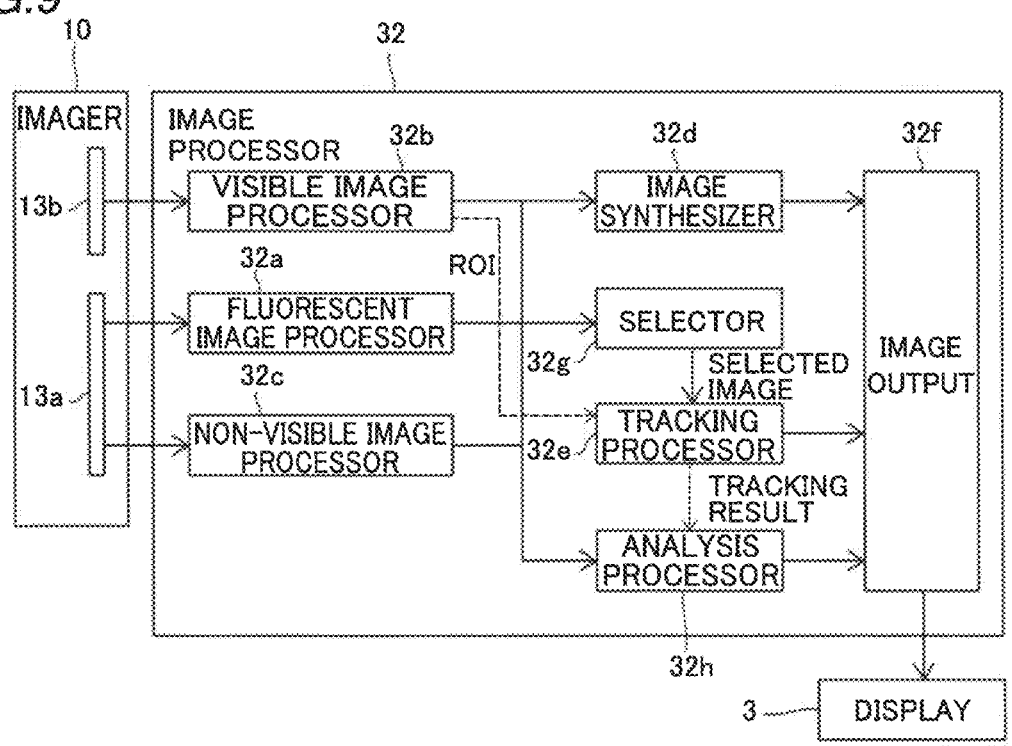

MOVING-BODY TRACKING AND TIME INTENSITY CURVE GENERATION PROCESSING

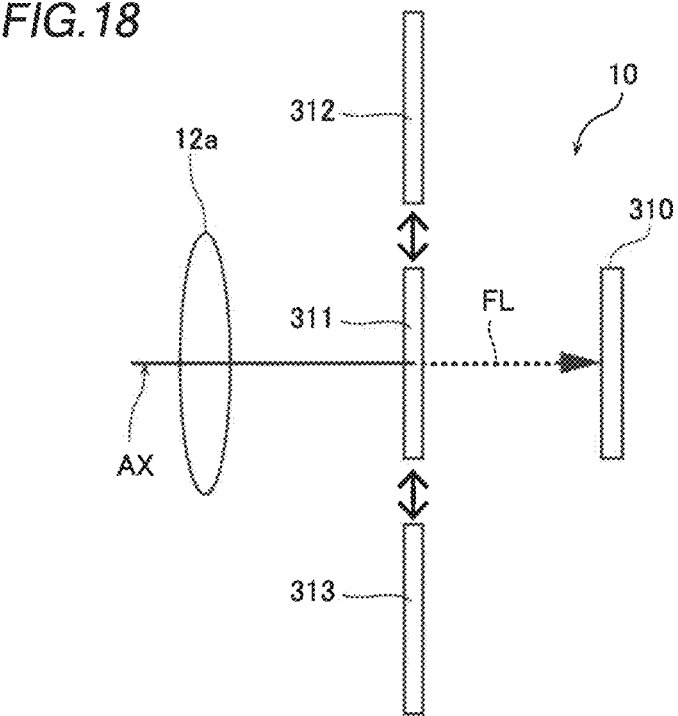

FLUORESCENT IMAGING DEVICE

CROSS-REFERENCE TO RELATED APPLICATIONS

This application claims the benefit of priority to Japanese Patent Application No. 2018-021597 filed on Feb. 9, 2018. The entire contents of this application are hereby incorporated herein by reference.

BACKGROUND OF THE INVENTION

Field of the Invention

The present invention relates to a fluorescent imaging device, and more particularly, it relates to a fluorescent imaging device that captures an image with a fluorescent agent administered to a subject

Description of the Background Art

A fluorescent imaging device that captures an image with a fluorescent agent administered to a subject is known in general, as disclosed in Japanese Patent No. 4745059, for example.

Japanese Patent No. 4745059 discloses a lymph node detecting apparatus (fluorescent imaging device) that radiates excitation light to a living body observation portion including lymph nodes into which a fluorescent agent is injected in advance and captures a fluorescent image via an optical filter that transmits fluorescence emitted from the living body observation portion.

Japanese Patent No. 4745059 further discloses that the optical filter transmits reflected light reflected by the living body observation portion, a reflected image reflected by the living body observation portion in addition to the fluorescent image is captured, and an observation image in which the fluorescent image and the reflected image are superimposed is obtained. In Japanese Patent No. 4745059, indocyanine green (hereinafter referred to as the ICG) is used as the fluorescent agent. The ICG generates fluorescence in a near-infrared wavelength band around 800 nm.

A fluorescent imaging device such as that disclosed in Japanese Patent No. 4745059 is used to visualize sentinel lymph nodes to be excised through a fluorescent image in sentinel lymph node biopsy. As another application example, the fluorescent imaging device can be used to check blood flow in a graft anastomotic site portion by passing a fluorescent agent through the graft anastomotic site to acquire a fluorescent image in coronary artery bypass graft surgery. In addition, the fluorescent imaging device is combined with an endoscopic device and can be used to check a surgical site or the like through a fluorescent image in endoscopic surgery.

In applications such as these, the movement of an observation site itself, the movement of an endoscope in the case of the endoscopic device, etc. occur, and thus it is desired to perform moving-body tracking processing on the observation site in a captured image. In the moving-body tracking processing, a feature in the observation site is used as a reference (mark), and the position of the observation site is detected from each image (moving image) continuously captured.

However, when the moving-body tracking processing is performed in the fluorescent imaging device, there are the following problems. When the moving-body tracking processing is performed using the fluorescent image, the observation site cannot be detected from the image unless the fluorescent agent has flowed into the observation site such that the fluorescence intensity sufficiently rises. When the moving-body tracking processing is performed using a reflected image of visible light, high-luminance luminescent spots may occur due to the reflected light of surgical lamps (so-called shadowless lamps) incorporated in the image. When luminescent spots occur at the observation site, an image of the observation site cannot be obtained, and the positions of the luminescent spots also change due to the movement of the observation site such that the accuracy of detecting the observation site is reduced.

Therefore, even when the fluorescent imaging device is used for surgical operations, for example, it is desired that the fluorescent imaging device can perform the moving-body tracking processing with a high degree of accuracy.

SUMMARY OF THE INVENTION

The present invention has been proposed in order to solve the aforementioned problems, and an object of the present invention is to provide a fluorescent imaging device capable of performing moving-body tracking processing with a high degree of accuracy even when the fluorescent imaging device is used for surgical operations, for example.

In order to attain the aforementioned object, a fluorescent imaging device according to an aspect of the present invention includes a light source unit including a first light source for radiating excitation light for a fluorescent agent administered to a subject, a second light source for radiating visible illumination light in a visible wavelength range, and a third light source for radiating non-visible light outside the visible wavelength range, an imager including an optical filter, the optical filter being configured to separate light in the visible wavelength range from both fluorescence outside the visible wavelength range excited by the excitation light and the non-visible light, the imager being configured to capture a fluorescent image based on the fluorescence, a visible image based on reflected light of the visible illumination light, and a non-visible image based on reflected light of the non-visible light, and a tracking processor that is operable to perform moving-body tracking for a region of interest that is set in an image based on at least the non-visible image.

In the present specification, the visible illumination light in the visible wavelength range indicates light having an intensity peak in the visible wavelength range, and it is allowed to include a wavelength component outside the visible wavelength range. Likewise, the non-visible light outside the visible wavelength range indicates light having an intensity peak in a non-visible wavelength range, and it is allowed to include a wavelength component in the visible wavelength range. That is, light generated from the light source unit has a wavelength spectrum that extends over a predetermined wavelength range corresponding to the light source unit, and thus the spectral skirt may exist across the visible range and the non-visible range. According to the JIS standards, for example, the visible wavelength range may be considered to have a short-wavelength limit of 360 nm to 400 nm and a long-wavelength limit of 760 nm to 830 nm.

As described above, the fluorescent imaging device according to this aspect of the present invention includes the imager including the optical filter, the optical filter being configured to separate the light in the visible wavelength range from both the fluorescence outside the visible wavelength range excited by the excitation light and the non-visible light, the imager being configured to capture the fluorescent image based on the fluorescence, the visible image based on the reflected light of the visible illumination light, and the non-visible image based on the reflected light of the non-visible light. Accordingly, the reflected light of a surgical lamp (shadowless lamp), which is the light in the visible wavelength range, is separated by the optical filter, and the non-visible image based on the reflected light of the non-visible light of the third light source can be acquired. Therefore, luminescent spots incorporated in the non-visible image due to the reflection of the surgical lamp can be significantly reduced or prevented. Furthermore, as to the non-visible light, a wavelength having different absorption characteristics or reflection characteristics between an observation site in the region of interest and the other sites of the subject is used, for example, such that the contrasting non-visible image in which the observation site and the other sites are distinguishable can be obtained without administering the fluorescent agent. In view of this, as described above, even when the fluorescent image before administration of the fluorescent agent cannot be obtained or the reflection of the surgical lamp is incorporated, the tracking processor can detect the region of interest from the image. Consequently, even when the fluorescent imaging device is used for surgical operations, for example, the moving-body tracking processing can be performed with a high degree of accuracy by the fluorescent imaging device.

In the aforementioned fluorescent imaging device according to this aspect, the tracking processor is preferably operable to perform the moving-body tracking for the region of interest based on the fluorescent image in addition to the non-visible image.

In the aforementioned fluorescent imaging device according to this aspect, the tracking processor is preferably operable to perform the moving-body tracking for the region of interest based on the non-visible image before administration of the fluorescent agent to the subject, and is preferably operable to perform the moving-body tracking for the region of interest based on the non-visible image or the fluorescent image after the administration of the fluorescent agent.

The aforementioned fluorescent imaging device according to this aspect preferably further includes a selector for selecting an image that is used for the moving-body tracking, the image being one of the fluorescent image, the non-visible image, and the visible image. Unless the luminescent spots due to the reflection of the surgical lamp are incorporated in the visible image, even the visible image can be used for the moving-body tracking. The selector is provided such that even when the fluorescent image before the administration of the fluorescent agent cannot be obtained or the reflection of the surgical lamp is incorporated, an appropriate image with which the moving-body tracking can be performed can be selected according to the situation.

The aforementioned fluorescent imaging device according to this aspect preferably further includes an analysis processor for analyzing flow of the fluorescent agent that is to pass through the region of interest in the fluorescent image based on the result of the moving-body tracking. According to this structure, even when the region of interest moves such as when blood flow in a graft anastomotic site is checked using the fluorescent agent in coronary artery bypass graft surgery, a time change (the flow of the fluorescent agent that is to pass through the region of interest) in the same region of interest of the subject can be grasped from the fluorescent image by the analysis processor based on the result of the moving-body tracking of the tracking processor. Consequently, even in the fluorescent imaging device, the flow of the fluorescent agent can be analyzed by image analysis using the result of the moving-body tracking. In the flow analysis by image analysis, there is a technique of analyzing the flow of a contrast agent by an X-ray imaging device with a gold marker placed in the vicinity of a region of interest as a marker, for example. According to the above structure, as compared with the case in which the X-ray imaging device is used, there are significant advantages such as the advantage of not causing radiation exposure by X-rays, the advantage of being minimally invasive because the placement of a mark such as a gold marker is not necessarily required, and the advantage of simplifying the device structure because an X-ray imaging device, which is likely to have a large-scale device structure, is not used.

In this case, the analysis processor is preferably operable to generate a time intensity curve of the fluorescence generated as a result of the flow of the fluorescent agent through the region of interest in the fluorescent image. According to this structure, with the time intensity curve that indicates a change over time in the flow of the fluorescent agent, the blood flow can be checked in the case of a blood vessel such as a coronary artery, and the lymph flow can be checked in the case of a lymphatic vessel, for example. Furthermore, even at the stage at which the fluorescence intensity is small (the rising edge immediately after the flow of the fluorescent agent into the region of interest or the falling edge after the concentration peak of the fluorescent agent), the moving-body tracking can be performed without the fluorescent image with low signal intensity but with the non-visible image, and thus the time intensity curve can be accurately acquired over a wide range from the rising edge to the falling edge of the fluorescence intensity. From the time intensity curve, various pieces of information useful for treatment and diagnosis can be obtained by analyzing various parameters such as an average flow rate, a slope, and transit time, and thus a highly accurate time intensity curve is useful for treatment, diagnosis, etc.

In the aforementioned structure including the selector, the selector is preferably operable to switch the image used for the moving-body tracking from the fluorescent image, the visible image, or the non-visible image during the moving-body tracking by the tracking processor. According to this structure, an image with which the moving-body tracking can be performed with a higher degree of accuracy can be selected according to the situation during the moving-body tracking, and thus the moving-body tracking processing can be performed with a higher degree of accuracy. For example, in the fluorescent image, the fluorescence intensity (the concentration of the fluorescent agent) is low at the stage immediately after the administration of the fluorescent agent or at the stage at which the fluorescent agent flows away from the region of interest such that the fluorescent image is not suitable, but high contrast can be obtained near the peak of the fluorescence intensity such that the moving-body tracking can be performed with a high degree of accuracy. Therefore, the fluorescent image, the visible image, or the non-visible image is switched during the moving-body tracking such that the moving-body tracking can be performed with a higher degree of accuracy using the switched image.

In the aforementioned structure in which the tracking processor is operable to perform the moving-body tracking based on the non-visible image before the administration of the fluorescent agent and is operable to perform the moving-body tracking based on the non-visible image or the fluorescent image after the administration of the fluorescent agent, the tracking processor is preferably operable to use the non-visible image as an image used for the moving-body tracking at least before the administration of the fluorescent agent and is preferably operable to switch the image used for the moving-body tracking to the fluorescent image based on a pixel value.

According to this structure, at the stage before the administration of the fluorescent agent with low fluorescence intensity (pixel value), the moving-body tracking can be performed using the non-visible image, and at the stage at which the fluorescence intensity (pixel value) is sufficiently high, the moving-body tracking can be performed with a high degree of accuracy using the fluorescent image. Consequently, the moving-body tracking can be performed with a high degree of accuracy by appropriate image selection before and after the administration of the fluorescent agent.

In the aforementioned fluorescent imaging device according to this aspect, the third light source is preferably configured to radiate the non-visible light in a near-infrared wavelength range. In the near-infrared wavelength range, the short-wavelength limit is the long-wavelength limit (760 nm to 830 nm) of visible light, and the long-wavelength limit is about 1400 nm to 2500 nm. It is known that near-infrared light tends to penetrate into living tissue and to be absorbed by hemoglobin in blood, for example. Therefore, when the non-visible image is based on the near-infrared light as described above, in the non-visible image, the blood vessel in which blood flows is relatively dark due to absorption, and regions other than the blood vessel is relatively bright such that even when the fluorescent agent is not administered, the contrasting non-visible image in which the blood vessel as the observation site and the other sites are distinguishable can be obtained. Therefore, when the blood vessel of the subject is imaged as the region of interest in particular, the moving-body tracking can be performed with a higher degree of accuracy.

In the aforementioned fluorescent imaging device according to this aspect, the third light source is preferably configured to radiate the non-visible light in a wavelength range that overlaps with a wavelength of the fluorescence, and the imager preferably includes a first imaging element for capturing the fluorescent image and the non-visible image and a second imaging element for capturing the visible image. According to this structure, using the wavelength range in which the wavelength of the fluorescence and the wavelength of the non-visible light overlap with each other, both the fluorescent image and the non-visible image can be captured by the common imaging element. Consequently, even when all of the fluorescent image, the non-visible image, and the visible image are captured, the device structure can be simplified.

In the aforementioned fluorescent imaging device according to this aspect, the third light source is preferably configured to radiate the non-visible light, which substantially excludes a wavelength range of light of a fluorescent lamp. In the present specification, the phrase "excludes (not including) a wavelength range of light of a fluorescent lamp" indicates that when the spectra of the third light source and the fluorescent lamp are compared, the spectra of the third light source and the fluorescent lamp do not overlap with each other at least in the wavelength range of half width (full width at half maximum), and it is allowed that the wavelength ranges of wavelength components of low intensity such as 20% or less of the peak intensity overlap with each other. According to this structure, the light (reflected light) of the surgical lamp in which the fluorescent lamp is generally used and the non-visible light of the third light source can be easily separated by the optical filter, and thus incorporation of the reflected light of the surgical lamp in the non-visible image is prevented as much as possible such that the image quality of the non-visible image can be improved. Consequently, the accuracy of the moving-body tracking using the non-visible image can be further improved.

In the aforementioned fluorescent imaging device according to this aspect, the tracking processor is preferably operable to perform the moving-body tracking of the region of interest via template matching performed between an image portion contained in an image and a template image. According to this structure, the moving-body tracking of the region of interest can be easily performed with a high degree of accuracy simply by preparing the template image in advance.

In this case, the tracking processor is preferably operable to perform processing of updating the template image with a captured image. According to this structure, even when the observation site in the region of interest is a blood vessel, a lymphatic vessel (lymph node), or a tumor, for example, and is deformed with an organic activity such as heartbeat, the template image is updated using the newly captured image such that robust moving-body tracking processing in which a reduction in accuracy can be significantly reduced or prevented can be performed even when the observation site in the region of interest is deformed.

In the aforementioned fluorescent imaging device according to this aspect, the imager is preferably configured to capture the fluorescent image, the visible image, and the non-visible image in the same field of view, and the tracking processor is preferably operable to perform the moving-body tracking of the region of interest of at least the non-visible image at the same position as that of the region of interest received on the visible image. According to this structure, the fluorescent image, the visible image, and the non-visible image are captured in the same field of view, and thus the site of the subject specified on the visible image represents the same sites in the fluorescent image and the non-visible image.

Therefore, a user can specify the region of interest on the same visible image as that actually viewed by the user, and the position coordinates of the specified region of interest can be directly used in the non-visible image such that the position coordinates of the region of interest can be easily acquired while the convenience for the user is ensured.

The aforementioned fluorescent imaging device according to this aspect preferably further includes an endoscopic device in which the light source unit and the imager are provided. According to this structure, even when fluorescent imaging is performed in the body of the subject, the moving-body tracking of the region of interest can be performed using the non-visible image. In the case of the endoscopic device, not only the region of interest in the subject but also the endoscope itself moves in the subject. Thus, the moving-body tracking of the region of interest including the observation site can be performed, and thus even when endoscopic biopsy is performed, for example, the fluorescent imaging device including the endoscopic device is particularly useful.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a timing chart illustrating lighting control of each light source.

FIG. 9 is a block diagram illustrating the structure of an image processor.

FIG. 18 is a schematic view showing a second modified example of the imager.

DESCRIPTION OF THE PREFERRED EMBODIMENTS

Embodiments of the present invention are hereinafter described with reference to the drawings.

First Embodiment

The structure of a fluorescent imaging device 100 according to a first embodiment of the present invention is now described with reference to FIGS. 1 to 11.

Figure 1:
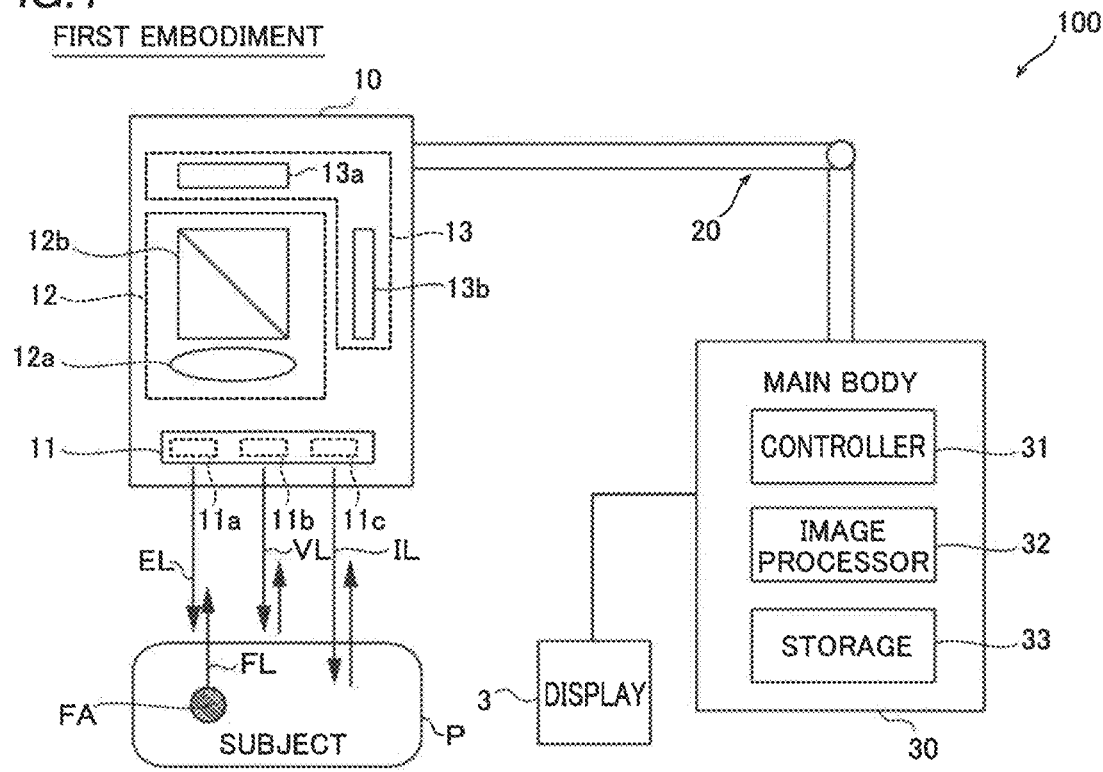
FIG. 1 is a diagram schematically showing the overall structure of a fluorescent imaging device according to a first embodiment.

As shown in FIG. 1, the fluorescent imaging device 100 according to the first embodiment radiates excitation light EL to detect fluorescence FL emitted from a fluorescent agent FA administered to a subject P and visualizes (images) an observation site of the subject P based on the fluorescence FL. In the first embodiment, the fluorescent imaging device 100 that images the observation site from the outside of the subject P by an imager 10 spaced apart from the subject P is described. The subject P is a living body, and a living body of a human, for example. The subject P may be a living body of a small animal such as a mouse.

Figure 2:
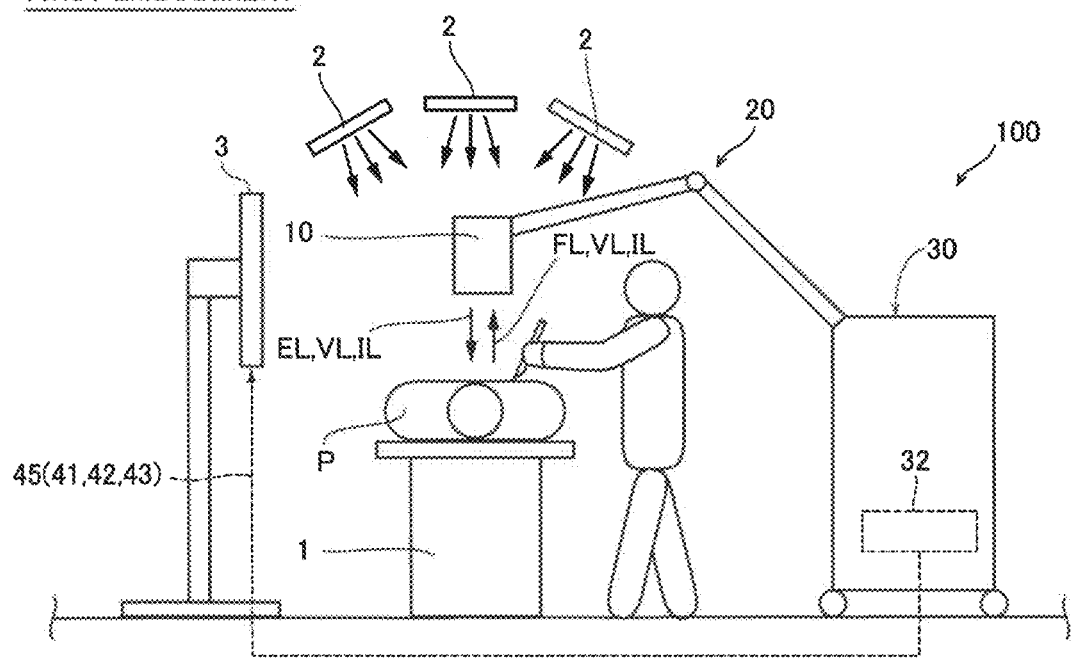
FIG. 2 is a diagram schematically showing an example in which the fluorescent imaging device is applied to a treatment support system used for surgical operations.

As shown in FIG. 2, the fluorescent imaging device 100 is used to check an observation site in surgical operations, for example. As an example, the fluorescent imaging device 100 used for cardiac surgical operations such as coronary artery bypass graft surgery is described below. Coronary artery bypass surgery is an operation to recover blood flow by connecting blood vessels to bypass a stenosed portion of a stenosed coronary artery. In the coronary artery bypass graft surgery, a doctor forms a bypass pathway of a coronary artery by anastomosing a bypass blood vessel called a graft to the artery of the opened heart. After the anastomosis, the doctor checks the blood flow of the graft, and then performs necessary treatment and closes the chest. When the blood flow of the graft is checked, the fluorescent agent FA is administered (injected) into the blood vessel on the upstream side of the graft. The fluorescent imaging device 100 can visualize (image) a state in which the fluorescent agent FA flows into and out of the graft by detecting the fluorescence FL from the fluorescent agent FA sent to the graft through the blood flow.

In FIG. 2, the subject P is placed on an operating table 1. Above the operating table 1, shadowless lamps 2, which are visible light illumination lamps for surgery, are disposed. The shadowless lamps 2 radiate visible light to a surgical field from multiple directions so as not to cause a shadow. The fluorescent imaging device 100 captures an image of the observation site by the imager 10 disposed at a position at which the surgical field can be imaged above the subject P. In FIG. 2, the fluorescent imaging device 100 is connected to a display 3, and outputs the captured image to the display 3.

The display 3 displays the image of the subject P output from the fluorescent imaging device 100. The display 3 is a monitor such as a liquid crystal display. In this manner, the fluorescent imaging device 100 and the display 3 constitute a treatment support system for surgical operations that captures and displays a fluorescent image. When the blood flow of the graft is checked, a user can check the image displayed on the display 3.

(Structure of Fluorescent Imaging Device)

As shown in FIG. 1, the fluorescent imaging device 100 according to the first embodiment includes the imager 10, an arm mechanism 20, and a main body 30 housed in a housing. A first end of the arm mechanism 20 is connected to the main body 30, and the arm mechanism 20 supports the imager 10 connected to a second end thereof and can hold the imager 10 at an arbitrary position and orientation within its movable range.

(Imager)

The imager 10 includes a light source 11 that radiates illumination light for imaging to the subject P, an optical system 12 through which light that enters the imager 10 passes, and an optical receiver 13 that receives light that enters the imager 10 and generates an image signal.

Figure 3:
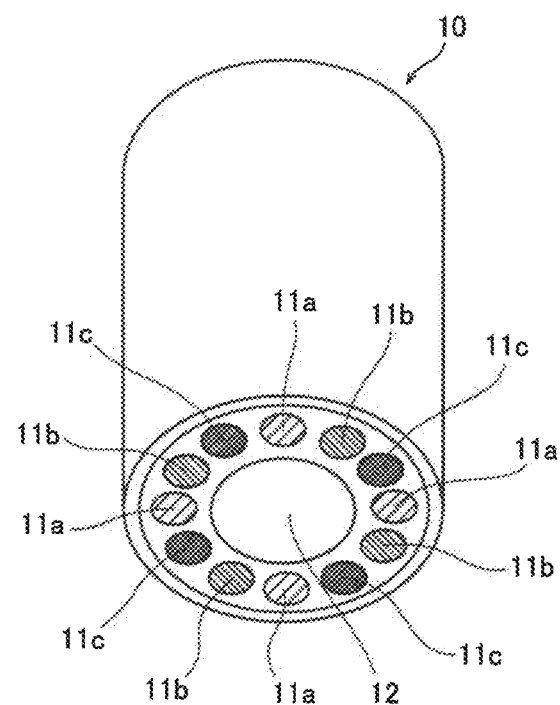
FIG. 3 is a schematic view of an imager including light sources.

The light source 11 includes a first light source 11a, a second light source 11b, and a third light source 11c. The first light source 11a radiates the excitation light EL for the fluorescent agent FA administered to the subject. The second light source 11b radiates visible illumination light VL in the visible wavelength range. The third light source 11c radiates non-visible light IL outside the visible wavelength range. These light sources each include a laser diode (LD) or a light-emitting diode (LED), for example. One or more first light sources 11a, one or more second light sources 11b, and one or more third light sources 11c are provided. FIG. 3 shows an example in which four first light sources 11a, four second light sources 11b, and four third light sources 11c are disposed. In FIG. 3, the first light sources 11a, the second light sources 11b, and the third light sources 11c are annularly disposed so as to surround, at an end of the imager 10, the periphery of the optical system 12 disposed at the central portion.

The first light sources 11a radiate the excitation light EL having an appropriate wavelength according to the light absorption characteristics of the fluorescent agent FA. As an example, the fluorescent agent FA is indocyanine green (ICG). The ICG has an absorption peak in a wavelength range of about 750 nm or more and less than about 800 nm, and emits the fluorescence FL (see FIG. 5) having a peak in a wavelength range of about 800 nm or more and less than about 850 nm when excited. The first light sources 11a radiate the excitation light EL (see FIG. 5) having a peak at about 750 nm, for example. Note that the fluorescent agent FA may be other than ICG.

The second light sources 11b radiates white light as the visible illumination light VL, for example. The white light includes a wavelength component (see FIG. 5) that extends over the substantially entire visible wavelength range. The visible illumination light VL may include a wavelength component outside the visible wavelength range, but the intensity of the wavelength component outside the visible wavelength range is sufficiently weaker than the intensity of the fluorescence FL or the non-visible light IL from the third light sources 11c.

As the non-visible light IL of the third light sources 11c, light of a wavelength outside the visible wavelength range and a wavelength in which absorption characteristics or reflection characteristics are different between the observation site and the other sites of the subject is selected. When the blood vessel in the graft anastomotic site as the observation site is imaged, light in the near-infrared wavelength range (near-infrared light), which tends to penetrate into living tissue and to be absorbed by hemoglobin in blood, is preferable as the non-visible light IL. In the first embodiment, the third light sources 11c radiate the non-visible light IL in the near-infrared wavelength range. The third light sources 11c radiate the non-visible light IL (see FIG. 5) having a peak M (see FIG. 5) in a wavelength range of about 800 nm or more and less than about 850 nm, for example. Therefore, the third light sources 11c radiate the non-visible light IL in a wavelength range (about 800 nm or more and less than about 850 nm) that overlaps with the wavelength of the fluorescence FL. In addition, the third light sources 11c radiate the non-visible light IL substantially not including the wavelength range (see FIG. 5) of light of fluorescent lamps (surgical lamps). That is, in FIG. 5, the upper limit of the light of the fluorescent lamps is about 600 nm at full width half maximum. On the other hand, the third light sources 11c each have a peak of about 800 nm or more and less than about 850 nm, and radiate the non-visible light IL having a lower limit of a half-value width of about 700 nm or more and less than 800 nm, for example.

Figure 4:
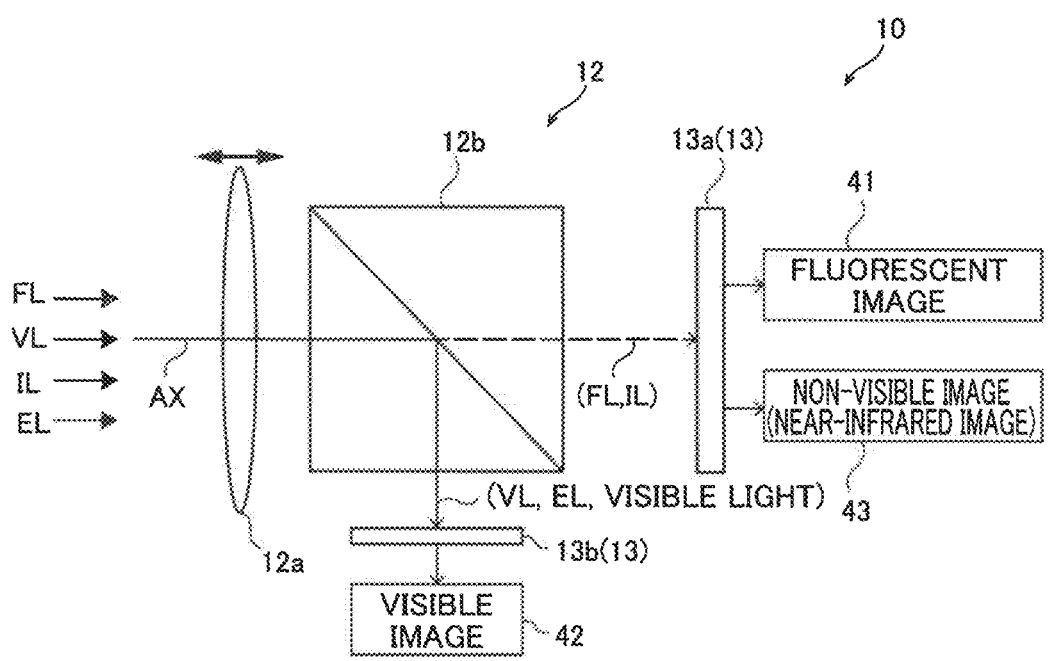
FIG. 4 is a schematic view illustrating the structure of the imager.

As shown in FIG. 4, the optical receiver 13 includes a first imaging element 13a that captures a fluorescent image 41 and a non-visible image 43, and a second imaging element 13b that captures a visible image 42. In the first embodiment, the common first imaging element 13a can capture both the fluorescent image 41 and the non-visible image 43. Each of the first imaging element 13a and the second imaging element 13b includes a solid-state imaging element such as a CMOS (Complementary Netal Oxide Semiconductor) image sensor or a CCD (Charge Coupled Device) image sensor. The second imaging element 13b can capture the visible image 42 as a color image using the visible illumination light VL, which is white light. The first imaging element 13a can capture the fluorescent image 41 and the non-visible image 43 as gray scale images, for example.

The optical system 12 includes a zoom lens 12a and an optical filter 12b. The optical system 12 focuses the light that enters the imager 10 on the optical receiver 13. Furthermore, the optical system 12 separates the reflected light of the visible illumination light VL reflected from the subject P and both the fluorescence FL emitted from the fluorescent agent FA and the reflected light of the non-visible light IL.

The zoom lens 12a can reciprocate in a direction of an optical axis AX by a lens moving mechanism (not shown), and performs focus adjustment. The optical filter 12b is placed between the zoom lens 12a and the optical system (the first imaging element 13a and the second imaging element 13b). In an example of FIG. 4, the optical filter 12b includes a prism beam splitter. The optical filter 12b has a function of selectively transmitting light of a specific wavelength and reflecting light of the other wavelengths. Thus, the optical filter 12b separates the light in the visible wavelength range and both the fluorescence FL outside the visible wavelength range excited by the excitation light EL and the non-visible light IL.

Figure 5:
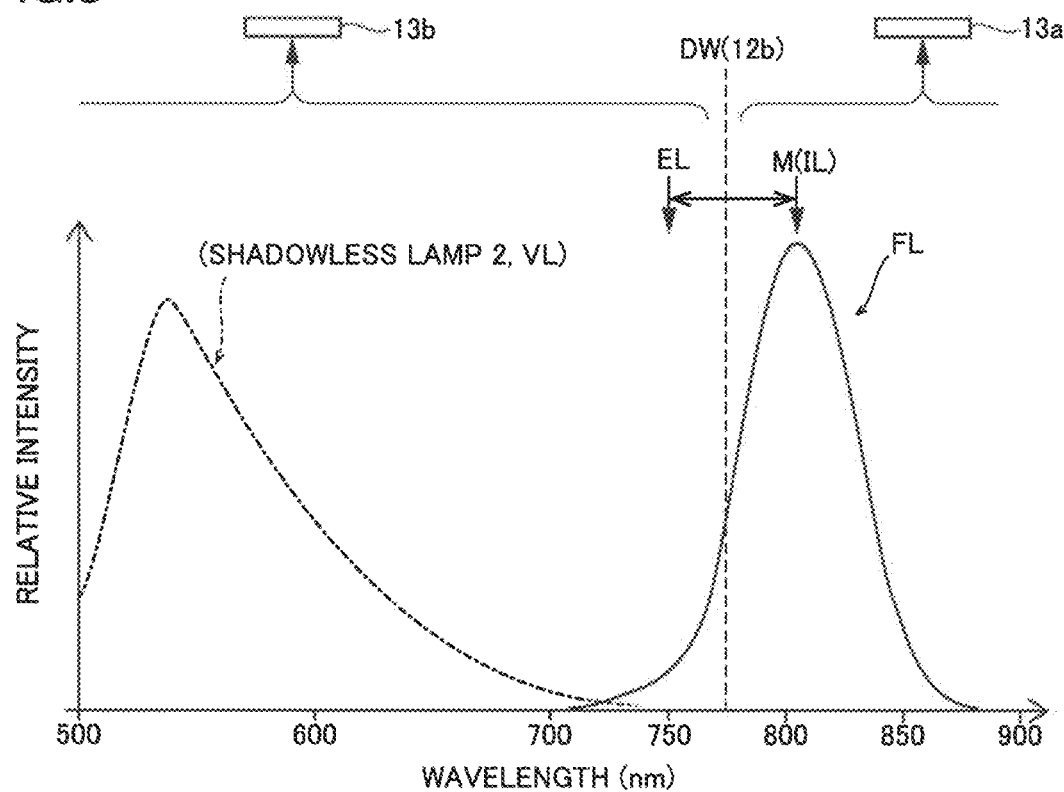
FIG. 5 is a diagram showing the spectrum of light separated by an optical filter.

As shown in FIG. 5, the optical filter 12b reflects the light in the visible wavelength range such as the reflected light of the visible illumination light VL and the reflected light of the shadowless lamps 2 and the excitation light EL, and projects the same onto the second imaging element 13b. The optical filter 12b transmits the fluorescence FL and the non-visible light IL outside the visible wavelength range, and projects the same onto the first imaging element 13a. That is, the optical filter 12b selectively transmits light having a predetermined wavelength DW or more (the fluorescence FL and the non-visible light IL) with the predetermined wavelength DW between the wavelengths of the visible light and the excitation light EL and the wavelengths of the fluorescence FL and the non-visible light IL as a boundary, and reflects light having less than the predetermined wavelength DW (the reflected light of the visible illumination light VL, the reflected light of the shadowless lamps 2, and the reflected light of the excitation light EL).

The first imaging element 13a and the second imaging element 13b detect the reflected light of the visible illumination light VL, the fluorescence FL, and the reflected light of the non-visible light IL via the common optical system 12.

Figure 6:
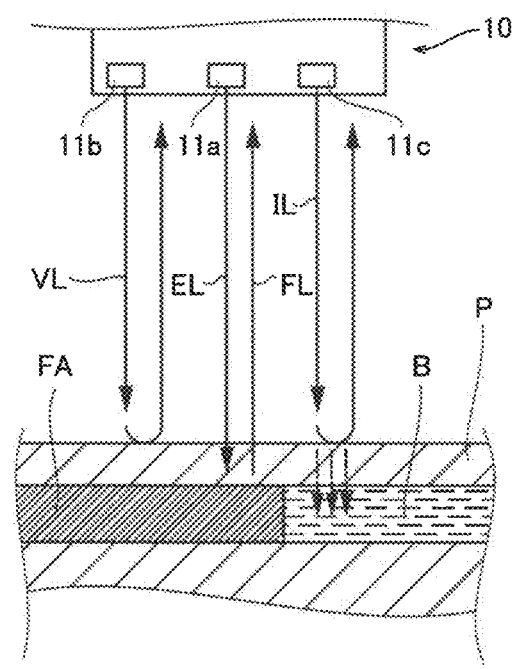
FIG. 6 is a diagram schematically illustrating light emitted from each light source and an image to be captured.

As shown in FIG. 6, the excitation light EL emitted from the first light sources 11a is partially reflected (not shown) by a surface of the subject P, and partially penetrates into the subject P. The excitation light EL is absorbed by the fluorescent agent FA when the fluorescent agent FA is administered. Consequently, the fluorescence FL is generated from the fluorescent agent FA, and enters the optical system 12. The incident fluorescence FL is transmitted through the optical filter 12b (see FIG. 4) and is imaged by the first imaging element 13a (see FIG. 4). Consequently, the fluorescent image 41 based on the fluorescence FL is acquired.

The visible illumination light VL radiated from the second light sources 11b is mainly reflected by the surface of the subject P, and enters the optical system 12. The reflected light of the incident visible illumination light VL is reflected by the optical filter 12b (see FIG. 4) and is imaged by the second imaging element 13b (see FIG. 4). Consequently, the visible image 42 based on the reflected light of the visible illumination light VL is acquired.

The near-infrared non-visible light IL radiated from the third light sources 11c tends to penetrate into the living tissue such that the same is reflected by the surface and the inside of the subject P, and the reflected light enters the optical system 12. The reflected light of the incident non-visible light IL passes through the optical filter 12b, and is imaged by the first imaging element 13a. Consequently, the non-visible image 43 based on the reflected light of the non-visible light IL is acquired.

Thus, the imager 10 captures the fluorescent image 41 based on the fluorescence FL, the visible image 42 based on the reflected light of the visible illumination light VL, and the non-visible image 43 based on the reflected light of the non-visible light IL.

Figure 7A:
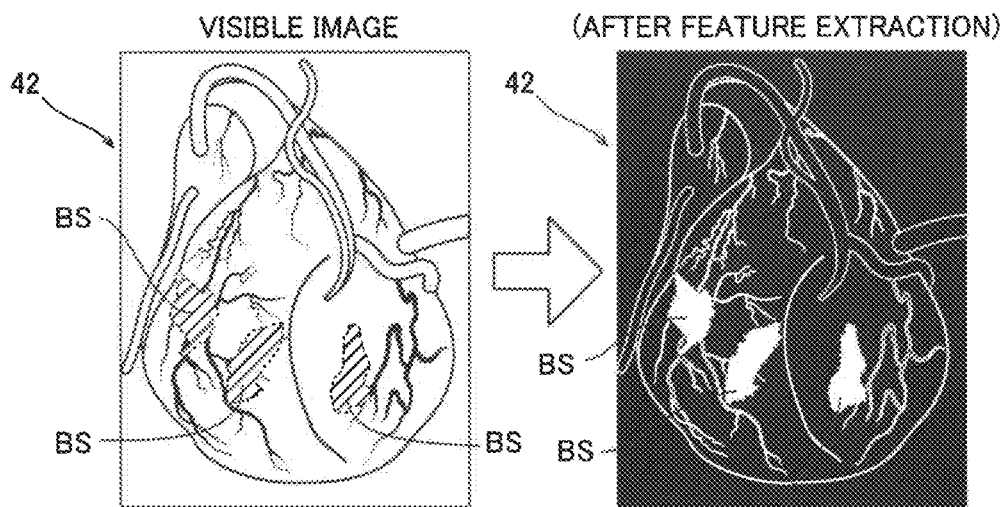
FIG. 7A is a schematic view of a visible image before and after feature extraction.
Figure 7B:
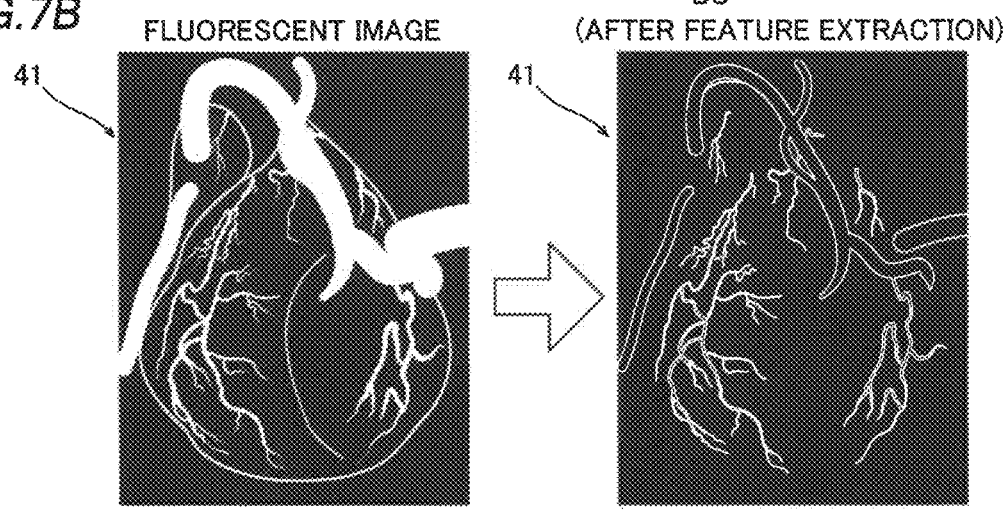
FIG. 7B is a schematic view of a fluorescent image before and after feature extraction.
Figure 7C:
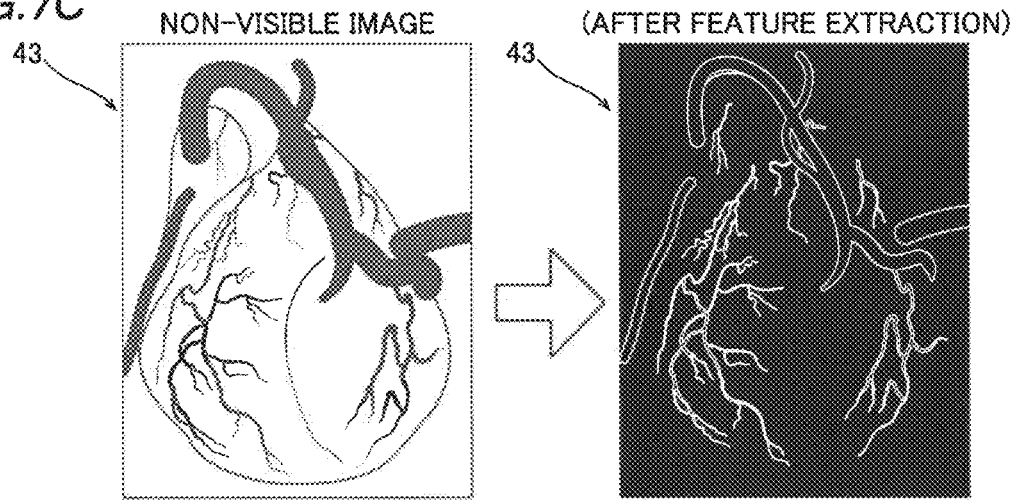
FIG. 7C is a schematic view of a non-visible image before and after feature extraction.

As shown in FIG. 7A, as the visible image 42, a color image similar to the observation site viewed by the user is obtained. As shown in FIG. 7B, as the fluorescent image 41, an image that contrasts in such a manner that the pixel value increases as the concentration of the fluorescent agent FA increases is obtained. FIG. 7B shows an example in which the fluorescent agent FA exists in the entire blood vessel for the sake of convenience, but actually, only a portion of the blood vessel in which the fluorescent agent FA exists becomes brighter. As shown in FIG. 7C, as the non-visible image 43, an image that contrasts between the blood vessel and a portion other than the blood vessel and the blood vessel portion and that reflects a difference in the absorption characteristics of the non-visible light IL between the blood vessel and the portion other than the blood vessel is obtained. That is, the non-visible light IL in the near-infrared wavelength range tends to be absorbed by hemoglobin in the blood, and thus the non-visible image 43 is obtained in such a manner that the pixel value of the blood vessel through which the blood B (see FIG. 6), which tends to relatively absorb the non-visible light IL, flows, is smaller, and the pixel value of the portion other than the blood vessel, which tends not to relatively absorb the non-visible light IL, is larger.

These images are obtained based on the light that enters the common optical system 12 (see FIG. 4) and is separated, and thus the same are images of the same field of view. That is, the imager 10 captures the fluorescent image 41, the visible image 42, and the non-visible image 43 in the same field of view.

(Main Body)

Returning to FIG. 1, the main body 30 includes a controller 31, an image processor 32, and a storage 33. The main body 30 also includes an operation unit (not shown) that receives a user's operation input to the controller 31. The main body 30 has a structure in which a PC (Personal Computer) is built in the wagon-type housing (see FIG. 2), for example.

The controller 31 controls the start and stop of radiation of the light (the excitation light EL, the visible illumination light VL, and the non-visible light IL) from the light source 11, for example, based on the input operation via the operation unit. The controller 31 outputs an image generated by the image processor 32 to the display 3. The controller 31 includes a processor such as a CPU (Central Processing Unit), for example.

As shown in FIG. 8, the controller 31 controls the lighting timings of the first light sources 11a, the second light sources 11b, and the third light sources 11c during imaging by the fluorescent imaging device 100. Specifically, the controller 31 performs control of turning on (ON) the second light sources 11b that radiate the visible illumination light VL at all timings. On the other hand, the controller 31 performs control of alternately and repeatedly turning on (ON) and turning off (OFF) the first light sources 11a that radiate the excitation light EL and the third light sources 11c that radiate the non-visible light IL at a predetermined time interval T.

The time interval T can be arbitrarily set, and can be equal to the frame rate of signal readout of the first imaging element 13a, for example. The frame rate is 30 fps or more, for example. Consequently, the first imaging element 13a alternately acquires the fluorescent image 41 and the non-visible image 43 for each frame.

Returning to FIG. 1, the image processor 32 generates the fluorescent image 41 and the non-visible image 43 based on a signal detected by the first imaging element 13a. The image processor 32 also generates the visible image 42 based on a signal detected by the second imaging element 13b. The image processor 32 also generates a synthetic image 44 (see FIG. 11) obtained by synthesizing the fluorescent image 41 and the visible image 42. The image processor 32 includes a processor such as a GPU (Graphics Processing Unit) or an FPGA (Field-Programmable Gate Array) configured for image processing, for example.

The storage 33 stores various programs to cause the processors to function as the controller 31 and the image processor 32. The storage 33 stores the images (various images including the fluorescent image 41, the visible image 42, and the non-visible image 43) generated by the image processor 32, etc. The storage 33 includes a nonvolatile memory or a hard disk drive (HDD), for example.

(Structure of Image Processor)

As shown in FIG. 9, in the first embodiment, the image processor 32 includes a fluorescent image processor 32a, a visible image processor 32b, a non-visible image processor 32c, an image synthesizer 32d, a tracking processor 32e, an image output 32f, and a selector 32g. Furthermore, in the first embodiment, the image processor 32 includes an analysis processor 32h. These processors included in the image processor 32 include software as functional blocks realized by the processors that execute a program for image processing. When a processor such as an FPGA is used, each functional block is constructed in the processor. A dedicated processor (processing circuit) may be provided for each processor, and each processor may include individual hardware.

The fluorescent image processor 32a and the non-visible image processor 32c acquire image signals from the first imaging element 13a to generate the fluorescent image 41 and the non-visible image 43, respectively. The visible image processor 32b acquires an image signal from the second imaging element 13b to generate the visible image 42. In addition, the fluorescent image processor 32a, the visible image processor 32b, and the non-visible image processor 32c can perform publicly known correction processing such as filtering of noise removal.

Figure 11:
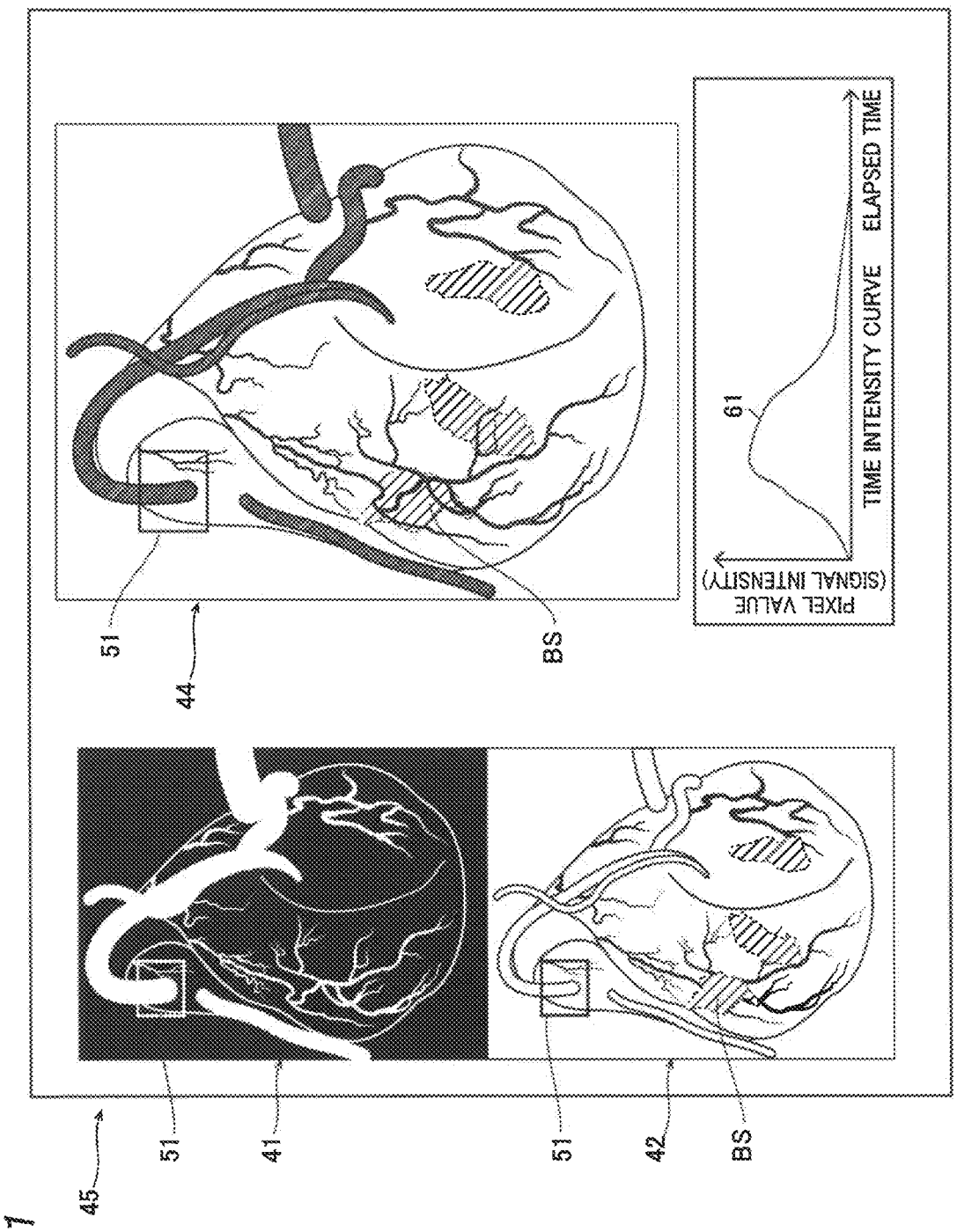
FIG. 11 is a diagram illustrating a screen image output to a display.

The image synthesizer 32d synthesizes the visible image 42 and the fluorescent image 41 to generate one synthetic image 44 (see FIG. 11). The synthesis is processing of superimposing the fluorescent image 41 on the visible image 42, for example. The image synthesizer 32d may synthesize the non-visible image 43 in addition to the visible image 42 and the fluorescent image 41.

The selector 32g selects an image used for moving-body tracking from among the fluorescent image 41, the visible image 42, and the non-visible image 43. For example, the selector 32g acquires the fluorescent image 41, the visible image 42, and the non-visible image 43 from the fluorescent image processor 32a, the visible image processor 32b, and the non-visible image processor 32c, respectively, and selects one or more images suitable for moving-body tracking from among the acquired images. The selector 32g outputs the image selected as an image used for moving-body tracking to the tracking processor 32e. The selection is performed according to the luminance value in the image, the elapsed time (the elapsed time from the administration of the fluorescent agent FA to the subject P, for example), and another preset selection criterion, for example. A selection method is described below in detail.

In the first embodiment, the tracking processor 32e performs moving-body tracking of a region of interest 51 (see FIG. 11) set in the image based on the image selected by the selector 32g. Specifically, the tracking processor 32e performs moving-body tracking of the region of interest 51 (see FIG. 14) by template matching between an image portion contained in the image and a template image 52 (see FIG. 14). The region of interest 51 is a region within a predetermined range specified by the user in the acquired image before the start of the moving-body tracking. The region of interest 51 is specified as a region including the observation site of interest in surgery. In the coronary artery bypass surgery, the range including the graft anastomotic site in which the blood flow is checked is set as the region of interest 51. The surrounding blood vessel including the graft anastomotic site changes its position and shape with heartbeat. Therefore, each time a frame image is newly acquired, the tracking processor 32e performs moving-body tracking to detect the position of the region of interest 51.

When the frame image selected by the selector 32g is newly acquired, the tracking processor 32e performs moving-body tracking and outputs the position coordinates of the region of interest 51 in the newly acquired frame image as the moving-body tracking result.

Figure 10:
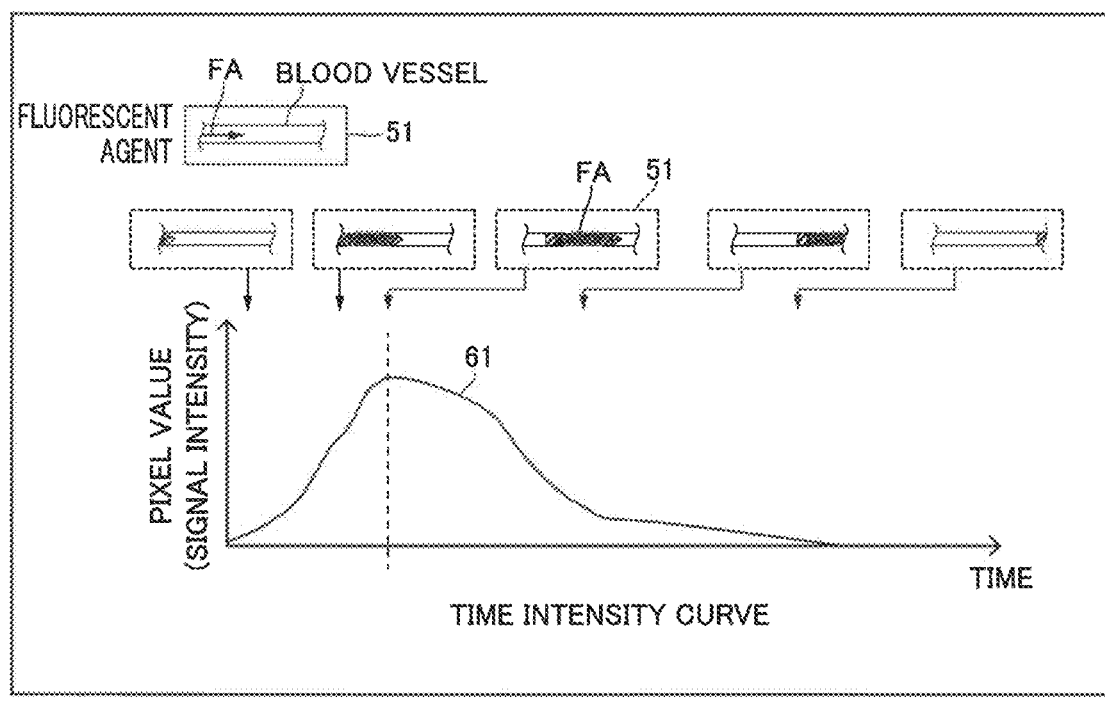
FIG. 10 is a diagram illustrating a time-intensity curve.

The analysis processor 32h analyzes the flow of the fluorescent agent FA that passes through the region of interest 51 in the fluorescent image 41 based on the moving-body tracking result. Specifically, as shown in FIG. 10, the analysis processor 32h generates a time intensity curve (TIC) 61 of the fluorescence FL caused by the fluorescent agent FA that flows through the region of interest 51 in the fluorescent image 41. In the coronary artery bypass surgery, the graft anastomotic site is set as the region of interest 51 such that the time intensity curve 61 of the fluorescence FL generated from the fluorescent agent FA that flows through the graft anastomotic site is generated. The time intensity curve 61 indicates a change in the concentration of the fluorescent agent FA that passes through the region of interest 51, and thus the same reflects the blood flow in the graft anastomotic site.

The analysis processor 32h acquires a pixel value in the region of interest 51 specified based on the moving-body tracking result from each frame image of the fluorescent image 41. As shown in FIG. 10, the analysis processor 32h generates the time intensity curve 61 by plotting temporal changes in the pixel value in the region of interest 51 in each frame image. The time intensity curve 61 is expressed in the form of a graph in which the vertical axis represents the pixel value of the fluorescent image 41, which is the signal intensity of the fluorescence FL, and the horizontal axis represents the elapsed time. Usually, the fluorescent agent FA is administered (injected) into the blood vessel from a position on the upstream side of the region of interest 51 and is carried to the region of interest 51 through the blood flow. When the fluorescent agent FA reaches the region of interest 51, the pixel value (fluorescence intensity) in the region of interest 51 gradually increases and reaches a peak at the predetermined timing. Then, the pixel value (fluorescence intensity) gradually decreases as the fluorescent agent FA passes through the region of interest 51. The time intensity curve 61 is a mountain-shaped curve with a peak. The fluorescent agent FA reaches the region of interest 51 in about 10 seconds, for example, although the fluorescent agent FA depends on a site (organ, place) to which the fluorescent agent FA is administered and the dose, and the concentration in the region of interest 51 reaches a peak in about 30 seconds.

Returning to FIG. 9, the image output 32f generates a screen image 45 (see FIG. 11) to be output to the display 3, using the processing results of the image synthesizer 32d, the tracking processor 32e, and the analysis processor 32h, and outputs the screen image 45. As shown in FIG. 11, the image output 32f generates the screen image 45 including the captured visible image 42 and fluorescent image 41 and the synthetic image 44 generated by the image synthesizer 32d, for example. Furthermore, the image output 32f displays the current position of the region of interest 51 in each image based on the moving-body tracking result of the tracking processor 32e. In FIG. 11, the rectangular region of interest 51 is superimposed and displayed on each image. The image output 32f includes the analysis result of the flow of the fluorescent agent FA by the analysis processor 32h in the screen image 45. In FIG. 11, the time intensity curve 61 as the analysis result of the flow is displayed side by side with each image. Therefore, in the screen image 45, the time intensity curve 61 is displayed as the analysis result of the blood flow in the region of interest 51 superimposed and displayed on the captured image.

(Processing Operations of Image Processor)

Figure 12:
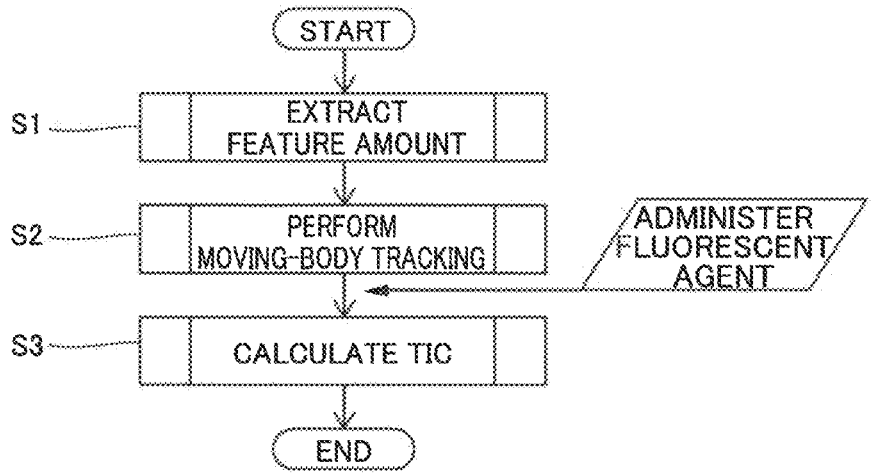
FIG. 12 is a flow diagram showing moving-body tracking and time intensity curve generation processing.

Operations of the moving-body tracking processing and the analysis processing of the time intensity curve 61 are now described. As shown in FIG. 12, when imaging starts, the image processor 32 performs processing of extracting a feature amount from the acquired frame image in step S1.

When the frame image (the fluorescent image 41, the visible image 42, or the non-visible image 43) is newly acquired, the selector 32g performs processing of extracting the feature amount from the image. The processing of extracting the feature amount is processing of extracting an edge in the image by image processing such as binarization processing and differential filtering, for example. A structural feature can be obtained from the image by extracting the feature amount in order to perform moving-body tracking.

On the right side of the drawings in FIGS. 7A to 7C, the results of the feature amount extraction processing for the fluorescent image 41, the visible image 42, and the non-visible image 43 are shown, respectively. In the coronary artery bypass surgery, the blood vessel including the graft anastomotic site is extracted by the feature amount extraction processing. Even in the visible image 42, the blood vessel that can be visually recognized from the outside can be extracted by the feature amount extraction processing. However, under the surgical illumination (the illumination of the shadowless lamps 2) in surgical operations, for example, the illumination light is incorporated, and luminescent spots BS that have gone white (the pixel value is saturated) occur in the visible image 42. In this case, when the feature amount extraction processing is performed on the visible image 42, the shapes of the luminescent spots BS are extracted as shown in FIG. 7A, and the shape of the blood vessel cannot be extracted. Thus, the accuracy of the moving-body tracking is reduced. On the other hand, the fluorescent image 41 and the non-visible image 43 are generated by the fluorescence FL and the non-visible light IL (reflected light) separated from the light in the visible light wavelength range by the optical filter 12b, and thus the moving-body tracking can be performed without being influenced by the surgical lamps. Furthermore, on the visible image 42 in which no illumination light is incorporated and no luminescent spots BS occur, the moving-body tracking can be performed.

Then, in step S2 of FIG. 12, the image processor 32 (tracking processor 32e) performs the moving-body tracking processing based on the image selected by the selector 32g from among the frame images (the fluorescent image 41, the visible image 42, and the non-visible image 43) from which the feature amount has been extracted.

(Moving-Body Tracking Processing)

The moving-body tracking processing is now described in detail with reference to FIGS. 13 and 14. The tracking processor 32e performs moving-body tracking in the set region of interest 51. The moving-body tracking processing is performed using the image (the fluorescent image 41, the visible image 42, or the non-visible image 43) after the feature amount extraction processing described above. An example in which the non-visible image 43 or the fluorescent image 41 is selected as an image used for moving-body tracking by the selector 32g is described below. For the sake of convenience, the non-visible image 43 or the fluorescent image 41 after the feature amount extraction processing is simply hereinafter referred to as the non-visible image 43 or the fluorescent image 41.

In step S11, the tracking processor 32e receives specification of the region of interest 51 (see FIG. 11) on the visible image 42 of the first frame (i=1). The letter i represents the frame number. Thus, the tracking processor 32e performs the moving-body tracking of the region of interest 51 of at least the non-visible image 43 at the same position as that of the region of interest 51 received on the visible image 42. As described above, the visible image 42 acquired in the same frame and the non-visible image 43 or the fluorescent image 41 are images of the same field of view, and thus the sites of the subject P indicated by the position coordinates in the image are the same. Therefore, setting of the region of interest 51 on the same visible image 42 as that viewed by the user is received, and the position coordinates (x, y) on the visible image 42 are applied to the non-visible image 43 or the fluorescent image 41 such that the region of interest 51 is set on the non-visible image 43 or the fluorescent image 41. The setting operation is performed by an input to the operation unit (not shown).

In step S12, the tracking processor 32e cuts out the image portion of the region of interest 51 and sets it as the template image 52 (see FIG. 14) for moving-body tracking for the (i+n)-th frame image (n is a positive integer). Immediately after specification of the region of interest 51 is received in step S11, the image of the region of interest 51 specified by the user is set as the template image 52 of the second frame (i=1, n=1).

In step S13, the tracking processor 32e performs template matching (see FIG. 14) between the template image 52 for the (i+n)-th frame and the newly acquired (i+n)-th frame image (the non-visible image 43 or the fluorescent image 41). The template matching is performed by calculating a cross-correlation coefficient R, for example.

Figure 14:
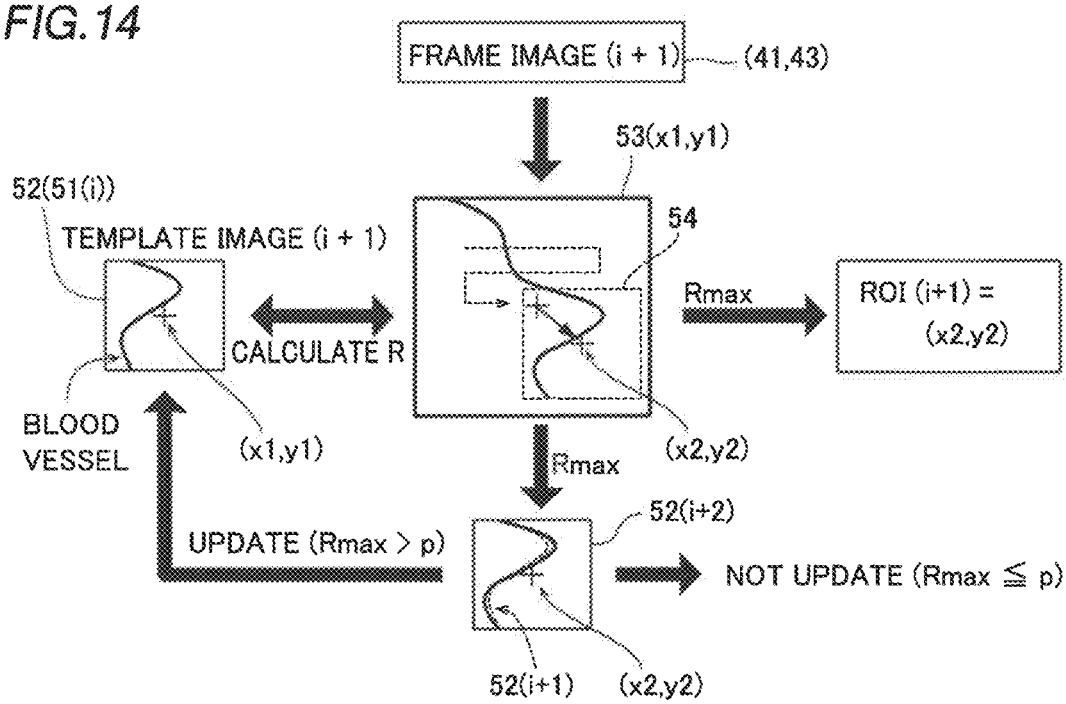
FIG. 14 is a schematic view illustrating template matching and template image update in the moving-body tracking processing.

As shown in FIG. 14, the tracking processor 32e sets a search range 53 centered on the center position coordinates (x1, y1) of the region of interest 51 in the i-th frame image as the (i+n)-th frame image. Here, an example of n=1 is shown. The search range 53 is set as a wider range than the template image 52 (i.e., the region of interest 51). The size of the search range 53 is set according to the moving speed and moving range of the blood vessel due to heartbeat and the frame rate of the acquired image such that in the newly acquired frame image (i+1), the region of interest 51 is included in the search range 53. Here, for the sake of convenience, it is assumed that when the template image 52 (region of interest 51) is set as a square region of 10 pixels×10 pixels, the search range 53 is set as a region of 20 pixels×20 pixels.

The tracking processor 32e sets a detection window 54 having the same size as the region of interest 51 in the search range 53 and calculates the cross-correlation coefficient R between the image portion in the detection window 54 and the template image 52. The tracking processor 32e moves the detection window 54 to calculate the cross-correlation coefficient R in the whole area within the search range 53. Then, the tracking processor 32e determines the position coordinates (x2, y2) at which the maximum cross-correlation coefficient Rmax is obtained as the position coordinates of the region of interest 51 in the (i+1)-th frame image. Thus, in step S13 of FIG. 13, the position coordinates (x2, y2) of the region of interest 51 in the (i+1)-th frame image are acquired.

Here, in the first embodiment, the tracking processor 32e performs processing of updating the template image 52 with the captured image. That is, the tracking processor 32e uses the image portion of the region of interest 51 having the maximum cross-correlation coefficient Rmax in the currently acquired frame image as the template image 52 for the frame image acquired in the next frame.

Specifically, in step S14, the tracking processor 32e compares the maximum cross-correlation coefficient Rmax obtained at the position coordinates (x2, y2) of the region of interest 51 in the (i+n)-th frame image with a predetermined threshold p. When the maximum cross-correlation coefficient Rmax is larger than the threshold p, the tracking processor 32e determines whether or not it is the last frame in step S14. When it is not the last frame, the tracking processor 32e returns to step S12, sets i+n to the frame number i, and updates the template image 52. For example, in the second (i+n=2) frame, when Rmax is larger than the threshold p, the template image 52 is updated with the second frame image.

That is, as shown in FIG. 14, when the maximum cross-correlation coefficient Rmax is larger than the threshold p, the tracking processor 32e cuts out the image portion of the region of interest 51 in which the maximum cross-correlation coefficient Rmax has been calculated, and updates it as the template image 52 for the next frame ((i+n+1)-th template image).

Therefore, as shown in FIG. 14, the shape of the feature amount (blood vessel) that appears in the template image 52 may differ between the (i+1)-th and (i+2)-th frames. Consequently, even when the shape of the blood vessel changes with heartbeat, the template image 52 is also changed (updated), following the change in the shape of the blood vessel.

Figure 13:
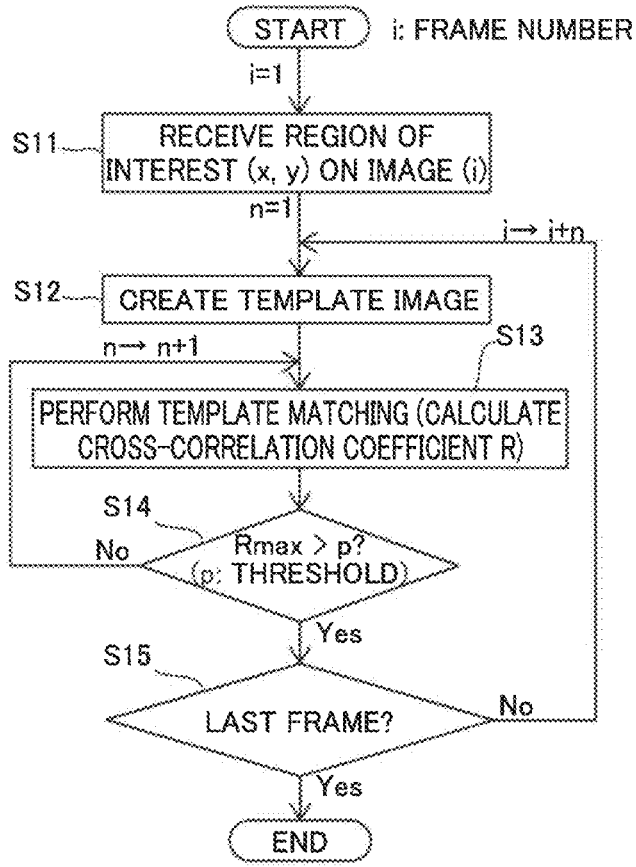
FIG. 13 is a flow diagram showing the details of moving-body tracking processing.

On the other hand, when the maximum cross-correlation coefficient Rmax is equal to or smaller than the threshold p in step S14 of FIG. 13, the tracking processor 32e returns to step S13 and sets n+1 to a variable n to perform template matching with the (i+n)-th template image 52. That is, when the maximum cross-correlation coefficient Rmax is equal to or smaller than the threshold p, the tracking processor 32e does not update the template image 52. For example, in the second (i+n=2) frame, when Rmax is equal to or smaller than the threshold p, the template image 52 for the second frame is directly used, and the region of interest 51 in the third (i+n=3) frame image acquired next is searched.

When the maximum cross-correlation coefficient Rmax is equal to or smaller than the threshold p, the similarity with the template image 52 is low, and there is a possibility that some kind of error may be included. Therefore, when Rmax is equal to or smaller than the threshold p, the template image 52 is not updated such that setting of an inappropriate image as the template image 52 can be prevented.

As described above, the moving-body tracking processing is performed.

Returning to FIG. 12, in step S3, the image processor 32 (analysis processor 32h) performs analysis processing of calculating the time intensity curve 61. At the stage before administration of the fluorescent agent FA, the time intensity curve 61 is not calculated (the fluorescence intensity is calculated as approximately 0).

The processing in step S1 to step S3 is executed each time a frame image is newly acquired after the start of moving-body tracking. Therefore, when the predetermined timing comes after the start of moving-body tracking, the user administers (injects) the fluorescent agent FA to the subject P. After the administration of the fluorescent agent FA, the fluorescence intensity (pixel value) changes in the fluorescent image 41, and thus the fluorescence intensity of the calculated time intensity curve 61 changes as shown in FIG. 10 in step S3.

(Selection of Image Used for Moving-Body Tracking)

An image (frame image) used for moving-body tracking (step S2 in FIG. 12) is now described. In the first embodiment, the selector 32g switches the image used for moving-body tracking from the fluorescent image 41, the visible image 42, or the non-visible image 43 during the moving-body tracking by the tracking processor 32e. Specifically, at least prior to the administration of the fluorescent agent FA, the selector 32g selects the non-visible image 43 as an image used for moving-body tracking, and switches the image used for moving-body tracking to the fluorescent image 41 based on the pixel value, for example.

Figure 15:
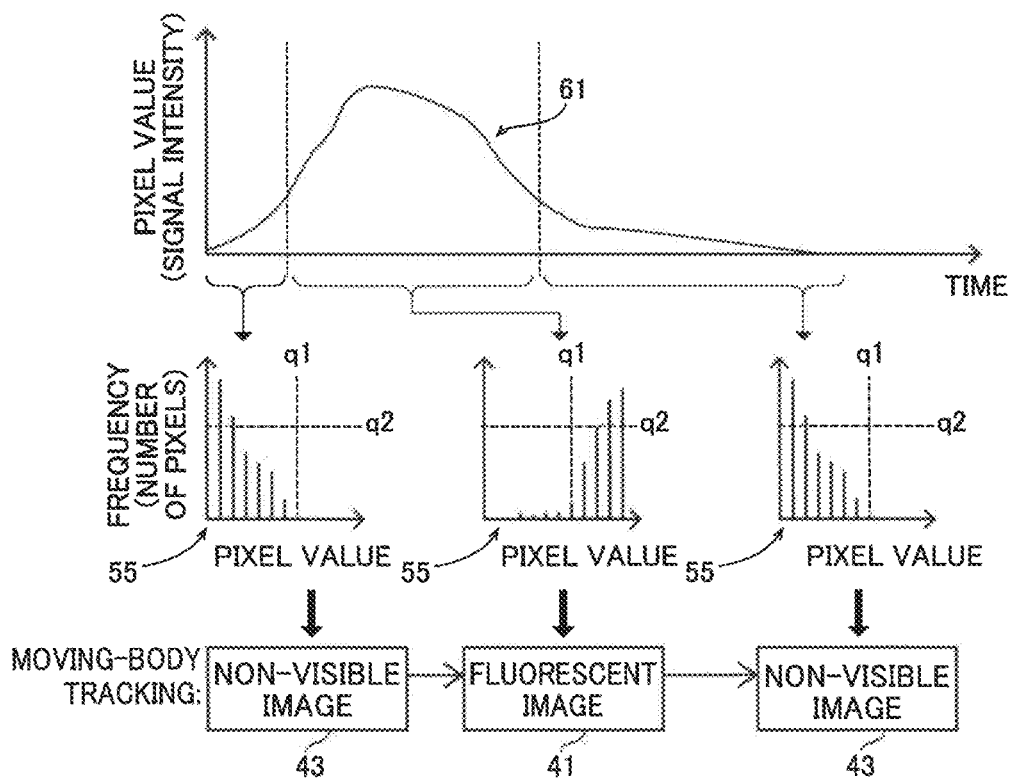
FIG. 15 is a schematic view illustrating control of switching images used for moving-body tracking according to a pixel value.

As shown in FIG. 15, the fluorescence intensity before and after the administration of the fluorescent agent FA in the region of interest 51 changes in the form of a mountain like the time intensity curve 61. The tracking processor 32e acquires a frequency distribution (histogram) 55 for each pixel value (fluorescence intensity) of the fluorescent image 41 acquired in each frame, for example. FIG. 15 shows the frequency distribution 55 in which the pixel value (fluorescence intensity) is taken on the horizontal axis and the frequency (number of pixels) is taken on the vertical axis. When the number of pixels, the pixel values (fluorescence intensity) of which exceed a predetermined value q1, exceeds a predetermined threshold q2, the tracking processor 32e switches the image used for moving-body tracking to the fluorescent image 41. When the number of pixels, the pixel values (fluorescence intensity) of which exceed the predetermined value q1, is equal to or less than the predetermined threshold q2, the tracking processor 32e switches the image used for moving-body tracking to the non-visible image 43. A value, at which the non-visible image 43 is switched to the fluorescent image 41 when the contrast of the fluorescent image 41 for feature amount extraction exceeds that of the non-visible image 43, is selected and set in advance as the predetermined threshold q2.

As described above, at the rising stage from before the flow of the fluorescent agent FA into the region of interest 51 to before the peak of the time intensity curve 61 and the falling stage at which the concentration of the fluorescent agent FA decreases after the peak of the time intensity curve 61, the number of pixels having a high pixel value (fluorescence intensity) decreases in the fluorescent image 41, and thus the tracking processor 32e performs moving-body tracking using the non-visible image 43. At the peak of the time intensity curve 61 at which the concentration of the fluorescent agent FA is high and the stage before and after the peak, the number of pixels having a high pixel value (fluorescence intensity) exceeds the predetermined threshold q2 in the fluorescent image 41, and thus the tracking processor 32e performs moving-body tracking using the fluorescent image 41.

<Modified Example of Selection of Image Used for Moving-Body Tracking>

FIG. 15 shows an example in which the selector 32g switches (selects) the image used for moving-body tracking based on the pixel value, but the selector 32g may select the image based on another piece of information other than the pixel value of the acquired frame image. For example, in a modified example, the selector 32g selects the non-visible image 43 as an image used for moving-body tracking before the administration of the fluorescent agent FA, and switches the image used for moving-body tracking to the fluorescent image 41 after the administration of the fluorescent agent FA. After the administration of the fluorescent agent FA, the timing at which the fluorescent agent concentration peaks in the region of interest 51 can be grasped in advance depending on the site (organ, place) to which fluorescent agent FA is administered and the dose, for example, as described above. Therefore, the selector 32g switches the image used for moving-body tracking at the preset timing based on the elapsed time after administration of the fluorescent agent FA, for example.

In the above description, an example is shown in which the image used for moving-body tracking is switched between the non-visible image 43 and the fluorescent image 41, but the selector 32g may select the visible image 42. As described above, when no luminescent spots BS occur in the image, the moving-body tracking can be performed using the visible image 42. Therefore, the selector 32g may select an image suitable for moving-body tracking from among the fluorescent image 41, the visible image 42, and the non-visible image 43.

(Advantageous Effects of First Embodiment)

According to the first embodiment, the following advantageous effects are achieved.

According to the first embodiment, as described above, the fluorescent imaging device 100 includes the imager 10 including the optical filter 12b that separates the light in the visible wavelength range and both the fluorescence FL and the non-visible light IL, and the imager 10 captures the fluorescent image 41, the visible image 42, and the non-visible image 43. Accordingly, the reflected light of the surgical lamps (shadowless lamps 2), which is the light in the visible wavelength range, is separated by the optical filter 12b, and the non-visible image 43 based on the reflected light of the non-visible light IL of the third light sources 11c can be acquired. Therefore, the luminescent spots BS incorporated in the non-visible image 43 due to the reflection of the surgical lamps can be significantly reduced or prevented. Furthermore, the contrasting non-visible image 43 in which the observation site and the other sites are distinguishable can be obtained based on the non-visible light IL without administering the fluorescent agent FA. In view of this, the selector 32g is provided to select an image used for moving-body tracking from among the fluorescent image 41, the visible image 42, and the non-visible image 43 such that even when the fluorescent image before administration of the fluorescent agent FA cannot be obtained or the reflection of the surgical lamps (shadowless lamps 2) is incorporated, an appropriate image with which the moving-body tracking can be performed can be selected according to the situation, and thus the tracking processor 32e can detect the region of interest 51 from the image. Consequently, even when the fluorescent imaging device 100 is used for surgical operations, for example, the moving-body tracking processing can be performed with a high degree of accuracy by the fluorescent imaging device 100.

According to the first embodiment, as described above, the fluorescent imaging device 100 includes the analysis processor 32h that analyzes the flow of the fluorescent agent FA that passes through the region of interest 51 in the fluorescent image 41 based on the moving-body tracking result. Accordingly, even when the region of interest 51 moves, a time change (the flow of the fluorescent agent FA that passes through the region of interest 51) in the same region of interest 51 of the subject can be grasped from the fluorescent image 41 by the analysis processor 32h based on the moving-body tracking result of the tracking processor 32e. Consequently, even in the fluorescent imaging device 100, the flow of the fluorescent agent FA can be analyzed by image analysis using the moving-body tracking result.

According to the first embodiment, as described above, the analysis processor 32h generates the time intensity curve (TIC) 61 of the fluorescence FL caused by the fluorescent agent FA that flows through the region of interest 51 in the fluorescent image 41. Accordingly, with the time intensity curve 61, the blood flow can be checked in the case of a blood vessel such as a coronary artery, and the lymph flow can be checked in the case of a lymphatic vessel, for example. Furthermore, even at the stage at which the fluorescence intensity is small (the rising edge immediately after the flow of the fluorescent agent FA into the region of interest 51 or the falling edge after the concentration peak of the fluorescent agent FA), the moving-body tracking can be performed without the fluorescent image 41 with low signal intensity but with the non-visible image 43, and thus the time intensity curve 61 can be accurately acquired over a wide range from the rising edge to the falling edge of the fluorescence intensity.

According to the first embodiment, as described above, during the moving-body tracking by the tracking processor 32e, the selector 32g switches the image used for moving-body tracking from the fluorescent image 41, the visible image 42, or the non-visible image 43. Accordingly, an image with which the moving-body tracking can be performed with a higher degree of accuracy can be selected according to the situation during the moving-body tracking, and thus the moving-body tracking processing can be performed with a higher degree of accuracy. As described above, high contrast can be obtained in the fluorescent image 41 near the peak of the fluorescence intensity other than the stage immediately after administration of the fluorescent agent FA or the stage at which the fluorescent agent FA flows away from the region of interest 51, and thus the moving-body tracking can be performed with a high degree of accuracy. Furthermore, when the reflection of the surgical lamps is not incorporated, the visible image 42 can also be used for moving-body tracking. Stable contrast can be obtained in the non-visible image 43 without being influenced by the presence or absence of administration of the fluorescent agent FA or the reflection of the surgical lamps. Therefore, the fluorescent image 41, the visible image 42, or the non-visible image 43 is switched during the moving-body tracking such that the moving-body tracking can be performed with a higher degree of accuracy using the switched image.

According to the first embodiment, as described above, the selector 32g selects the non-visible image 43 as an image used for moving-body tracking at least before administration of the fluorescent agent FA, and switches the image used for moving-body tracking to the fluorescent image 41 based on the pixel value. Accordingly, at the stage before administration of the fluorescent agent FA with low fluorescence intensity (pixel value), the moving-body tracking can be performed using the non-visible image 43, and at the stage at which the fluorescence intensity (pixel value) is sufficiently high, the moving-body tracking can be performed with a high degree of accuracy using the fluorescent image 41. Consequently, the moving-body tracking can be performed with a high degree of accuracy by appropriate image selection before and after administration of the fluorescent agent FA.

When the selector 32g selects the non-visible image 43 as an image used for moving-body tracking before administration of the fluorescent agent FA and switches the image used for moving-body tracking to the fluorescent image 41 after the administration of the fluorescent agent FA, the non-visible image 43 is switched to the fluorescent image 41 at the timing at which the fluorescence intensity (pixel value) is sufficiently high based on the elapsed time from the administration point of the fluorescent agent FA such that the moving-body tracking can be performed. Consequently, the moving-body tracking can be performed with a high degree of accuracy by appropriate image selection.

According to the first embodiment, as described above, the third light sources 11c radiate the non-visible light IL in the near-infrared wavelength range. Accordingly, in the non-visible image 43, the blood vessel in which blood flows is relatively dark due to absorption, and regions other than the blood vessel is relatively bright such that even when the fluorescent agent FA is not administered, the contrasting non-visible image 43 in which the blood vessel as an observation site and the other sites are distinguishable can be obtained. Therefore, when the blood vessel of the subject is imaged as the region of interest 51 in particular, the moving-body tracking can be performed with a higher degree of accuracy.

According to the first embodiment, as described above, the third light sources 11c radiate the non-visible light IL in the wavelength range that overlaps with the wavelength of the fluorescence FL, and the imager 10 includes the first imaging element 13a that captures the fluorescent image 41 and the non-visible image 43 and the second imaging element 13b that captures the visible image 42. Accordingly, using the wavelength range in which the wavelength of the fluorescence FL and the wavelength of the non-visible light IL overlap with each other, both the fluorescent image 41 and the non-visible image 43 can be captured by the common imaging element. Consequently, even when all of the fluorescent image 41, the non-visible image 43, and the visible image 42 are captured, the device structure can be simplified.

According to the first embodiment, as described above, the third light sources 11c radiate the non-visible light IL substantially not including the wavelength range of light of the fluorescent lamps. Accordingly, the light of the surgical lamps (shadowless lamps 2) in which the fluorescent lamps are generally used and the non-visible light IL of the third light sources 11c can be easily separated by the optical filter 12b, and thus incorporation of the reflected light of the surgical lamps in the non-visible image 43 is prevented as much as possible such that the image quality of the non-visible image 43 can be improved. Consequently, the accuracy of the moving-body tracking using the non-visible image 43 can be further improved.

According to the first embodiment, as described above, the tracking processor 32e performs moving-body tracking of the region of interest 51 by template matching between the image portion contained in the image and the template image 52. Accordingly, the moving-body tracking of the region of interest 51 can be easily performed with a high degree of accuracy simply by preparing the template image 52 in advance.

According to the first embodiment, as described above, the tracking processor 32e performs processing of updating the template image 52 with the captured image. Accordingly, even when the observation site in the region of interest 51 is deformed with an organic activity such as heartbeat, the template image 52 is updated using the newly captured image such that robust moving-body tracking processing in which a reduction in accuracy can be significantly reduced or prevented can be performed even when the observation site in the region of interest 51 is deformed.

According to the first embodiment, as described above, the imager 10 captures the fluorescent image 41, the visible image 42, and the non-visible image 43 in the same field of view, and the tracking processor 32e performs moving-body tracking of the region of interest 51 of at least the non-visible image 43 at the same position as that of the region of interest 51 received on the visible image 42. Accordingly, the user can specify the region of interest 51 on the same visible image 42 as that actually viewed by the user, and the position coordinates of the specified region of interest 5 can be directly used in the non-visible image 43 such that the position coordinates of the region of interest 51 can be easily acquired while the convenience for the user is ensured.

Second Embodiment

A second embodiment of the present invention is now described with reference to FIG. 16. In the second embodiment, a fluorescent imaging device 200 includes an endoscopic device 110, unlike the first embodiment in which imaging is performed from the outside of the subject P. The same structures as those of the first embodiment are denoted by the same reference numerals, and description thereof is omitted.

Figure 16:
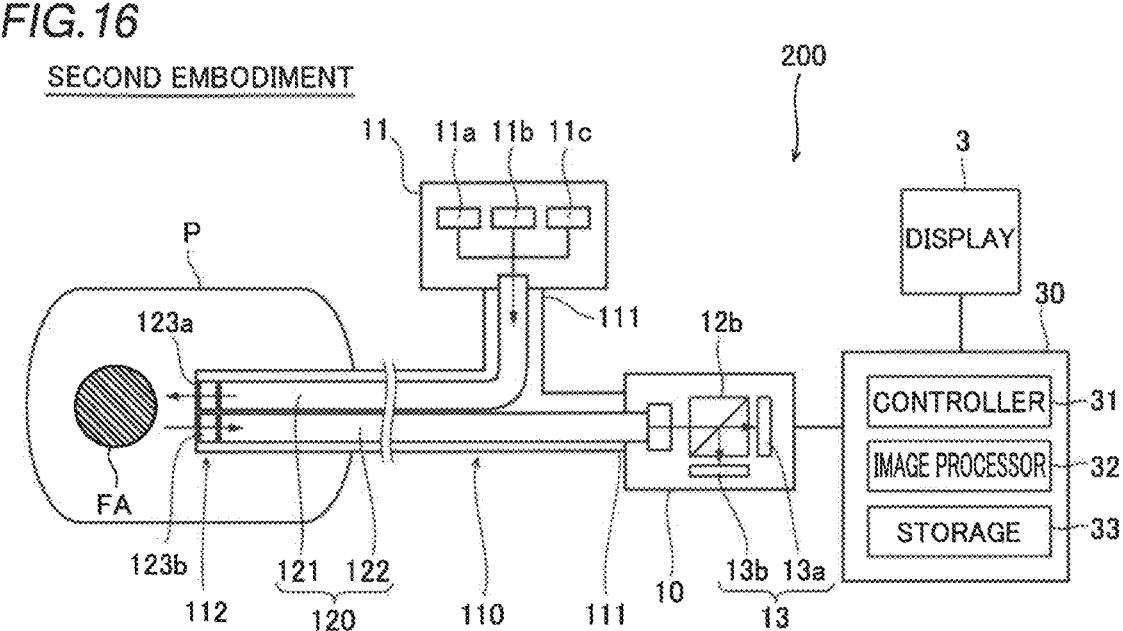
FIG. 16 is a schematic view showing the overall structure of a fluorescent imaging device according to a second embodiment.

As shown in FIG. 16, the fluorescent imaging device 200 according to the second embodiment includes the endoscopic device 110 including a light source 11 and an imager 10. The fluorescent imaging device 200 further includes a main body 30 connected to the endoscopic device 110.

The endoscopic device 110 includes a flexible and deformable cable 120. The cable 120 is connected to the light source 11 and the imager 10 at branched root portions 111. A distal end 112 of the cable 120 is inserted into a subject P and is carried to the vicinity of an observation site inside the subject P.

Inside the cable 120, a light-sending guide 121 and a light-receiving guide 122 are provided. The light-sending guide 121 and the light-receiving guide 122 are each a light guide including an optical fiber, for example.

The light-sending guide 121 is optically connected to the light source 11 at the root portion 111 and extends to the distal end 112. The light-sending guide 121 sends light emitted from the light source 11 to the distal end 112 and emits the light from the distal end 112 of the cable 120 via a lens 123a. The light-sending guide 121 is optically connected to each of a first light source 11a, a second light source 11b, and a third light source 11c of the light source 11, and can send excitation light EL, visible illumination light VL, and non-visible light IL radiated from the respective light sources to the distal end 112.

The light-receiving guide 122 is optically connected to the imager 10 at the root section 111 and extends to the distal end 112. The light-receiving guide 122 can send the light (the reflected light of the visible illumination light VL, fluorescence FL, and the reflected light of the non-visible light IL) received via a lens 123b at the distal end 112 to the imager 10 connected to the root portion 111.

The light sent to the imager 10 is separated by an optical filter 12b. That is, the fluorescence FL and the reflected light of the non-visible light IL pass through the optical filter 12b and are received by a first imaging element 13a, and the reflected light of the excitation light EL and the reflected light of the visible illumination light VL are reflected by the optical filter 12b and are received by a second imaging element 13b. The first imaging element 13a and the second imaging element 13b acquire a fluorescence image 41, a visible image 42, and a non-visible image 43.

The fluorescent image 41, the visible image 42, and the non-visible image 43 are acquired by an image processor 32. Using an image selected by a selector 32g (see FIG. 9), a tracking processor 32e (see FIG. 9) performs moving-body tracking of a region of interest 51. Furthermore, an analysis processor 32h (see FIG. 9) of the image processor 32 analyzes the flow of a fluorescent agent FA. The structure of the image processor 32 is similar to that according to the first embodiment. The image selection by the selector 32g, the moving-body tracking processing by the tracking processor 32e, and the analysis processing by the analysis processor 32h are similar to those according to the first embodiment. In the image processor 32, the visible image 42 and the fluorescent image 41 are synthesized by an image synthesizer 32d. The image processor 32 outputs the visible image 42, the fluorescent image 41, a synthetic image 44, and a screen image 45 including and a time intensity curve 61 to a display 3.

The remaining structures of the second embodiment are similar to those of the first embodiment.

In the second embodiment, the light source 11 (the first light source 11a, the second light source 11b, and the third light source 11c) may be incorporated in the distal end 112 of the cable 120. In this case, instead of the light-sending guide 121, a connecting wire that electrically connects the light source 11 to the main body 30 is provided in the cable 120. Similarly, the imager 10 (the first imaging element 13a and the second imaging element 13b) may be incorporated in the distal end 112 of the cable 120. In this case, instead of the light-receiving guide 122, a connecting wire that electrically connects the imager 10 to the main body 30 is provided in the cable 120.

(Advantageous Effects of Second Embodiment)

According to the second embodiment, the following advantageous effects are achieved.

In the endoscopic device 110, the distal end 112 moves and cannot keep a distance from the observation site constant (the radiation intensity of the illumination light to the observation site cannot be controlled), and thus there is a possibility that the reflected light of the visible illumination light VL is strongly incorporated in the visible image 42, and luminescent spots BS occur. Therefore, in the second embodiment, even when capturing of the visible image 42 and moving-body tracking are performed at the same time, incorporation of the luminescent points BS in the nonvisible image 43 due to reflection of the visible illumination light VL can be significantly reduced or prevented, similarly to the first embodiment. Furthermore, the moving-body tracking of the region of interest 51 set in the image is performed based on the contrasting non-visible image 43 in which the observation site and the other sites are distinguishable such that the region of interest 51 can be detected from the image without administering the fluorescent agent FA. Consequently, the region of interest 51 can be detected using the non-visible image 43 in which the influence of the reflected light is significantly reduced or prevented without administering the fluorescent agent FA, and thus even when the fluorescent imaging device 200 is used for endoscopic surgery, for example, the moving-body tracking processing can be performed with a high degree of accuracy by the fluorescent imaging device 200.

According to the second embodiment, as described above, the fluorescent imaging device 200 includes the endoscopic device 110 including the light source 11 and the imager 10. Accordingly, even when fluorescent imaging is performed in the body of the subject, the moving-body tracking of the region of interest 51 can be performed using the non-visible image 43. In the case of the endoscopic device 110, not only the region of interest 51 in the subject but also the endoscope itself moves in the subject. Thus the moving-body tracking of the region of interest 51 including an observation site that cannot be recognized in the visible image 42 can be performed, and thus even when endoscopic biopsy is performed, for example, the fluorescent imaging device 200 including the endoscopic device 110 is particularly useful.

The remaining advantageous effects of the second embodiment are similar to those of the first embodiment.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the analysis processor 32h that analyzes the flow of the fluorescent agent FA is provided in each of the aforementioned first and second embodiments, the present invention is not restricted to this.

According to the present invention, the analysis processor 32h may not be provided. The moving-body tracking is useful not only to analyze the flow of the fluorescent agent FA but also to specify an excision site on an image at the time of biopsy and to specify a treatment site, for example.

While as the analysis of the flow of the fluorescent agent FA, the analysis processor 32h generates the time intensity curve 61 of the fluorescence in each of the aforementioned first and second embodiments, the present invention is not restricted to this. The analysis processor 32h may alternatively perform any analysis processing other than generation of the time intensity curve 61 as long as processing of analyzing the flow of the fluorescent agent is performed by image analysis.

While the tracking processor 32e performs the moving-body tracking of the region of interest 51 based on the fluorescent image 41 in addition to the non-visible image 43 in each of the aforementioned first and second embodiments, the present invention is not restricted to this. The tracking processor 32e may alternatively perform the moving-body tracking based on only one of the fluorescent image 41, the visible image 42, and the non-visible image 43.

While the tracking processor 32e switches the image used for moving-body tracking to the non-visible image 43 or the fluorescent image 41 based on the pixel value in each of the aforementioned first and second embodiments, the present invention is not restricted to this. The tracking processor 32e may not switch the image used for moving-body tracking. The tracking processor 32e may alternatively perform moving-body tracking using both the non-visible image 43 and the fluorescent image 41. A synthetic image of the non-visible image 43 and the fluorescent image 41 may alternatively be created, and the moving-body tracking may alternatively be performed on the synthetic image. When the tracking processor 32e switches the image used for moving-body tracking, switching may alternatively be performed based on information other than the pixel value.

While the tracking processor 32e performs moving-body tracking by template matching in each of the aforementioned first and second embodiments, the present invention is not restricted to this. Any method other than template matching may alternatively be used as a method for the moving-body tracking by the tracking processor 32e. For example, the region of interest 51 set in the image may alternatively be detected by machine learning without using the template image 52.

While the tracking processor 32e performs processing of updating the template image 52 in each of the aforementioned first and second embodiments, the present invention is not restricted to this. The tracking processor 32e may not update the template image 52. For example, the tracking processor 32e may alternatively use only the image of the region of interest 51 initially specified by the user as the template image 52. When a slightly deformed site of the subject P is the region of interest 51, the region of interest 51 can be accurately detected without updating the template image 52.

While the third light source 11c radiates the non-visible light IL in the near-infrared wavelength range in each of the aforementioned first and second embodiments, the present invention is not restricted to this. The third light source 11c may alternatively radiate infrared light not in the near-infrared wavelength range as the non-visible light IL. Furthermore, the third light source 11c may alternatively radiate the non-visible light IL having a wavelength in an ultraviolet range on the short wavelength side relative to the visible wavelength range. As described above, the wavelength of the non-visible light IL need only be a wavelength having different absorption characteristics or reflection characteristics between the observation site in the region of interest and the other sites of the subject, and thus the feature amount with which the observation site in the region of interest is identified can be extracted by image processing.

Figure 17:
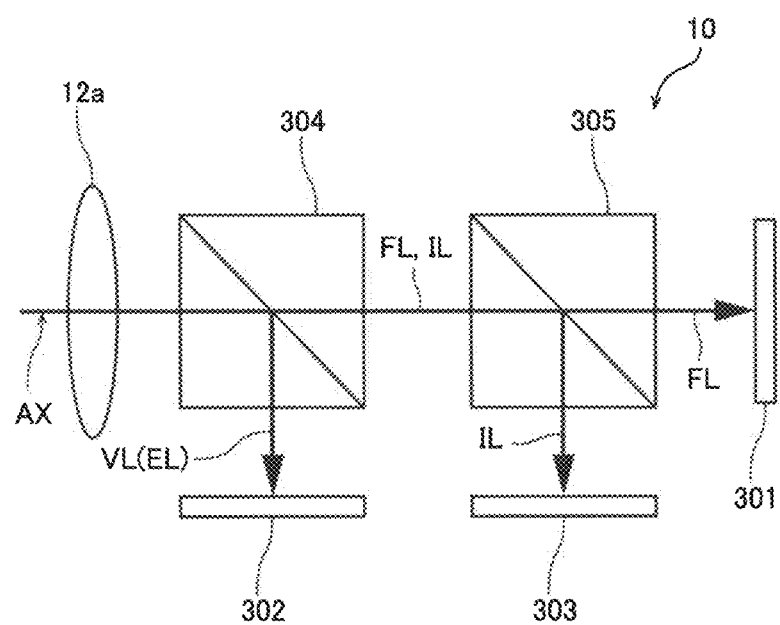
FIG. 17 is a schematic view showing a first modified example of the imager.

While the third light source 11c radiates the non-visible light IL in the wavelength range that overlaps with the wavelength of the fluorescence FL in each of the aforementioned first and second embodiments, the present invention is not restricted to this. The non-visible light IL and the fluorescence FL may alternatively have different peak wavelengths, and the wavelength ranges may not overlap with each other. Furthermore, the fluorescent image 41 and the non-visible image 43 may not be captured by the common first imaging element 13a. In this case, as in a first modified example shown in FIG. 17, a fluorescence imaging element 301, a visible light imaging element 302, and a non-visible light imaging element 303 may be separately provided. In the first modified example, a first optical filter 304 that separates visible light (including excitation light EL and the illumination light of shadowless lamps 2, for example) and non-visible light (including fluorescence FL and non-visible light IL) and a second optical filter 305 that separates the fluorescence FL and the non-visible light IL are provided.

In addition to this, as in a second modified example shown in FIG. 18, a fluorescence filter 311 that selectively transmits light in the wavelength range of fluorescence FL, a visible light filter 312 that selectively transmits light in the wavelength range of visible illumination light VL, and a non-visible light filter 313 that selectively transmits light in the wavelength range of non-visible light IL may be provided, and these filters may be alternately moved on the optical path of a common (single) imaging element 310. Thus, each of a fluorescent image 41, a visible image 42, and a non-visible image 43 can be captured by the common imaging element 310.

While the tracking processor 32e receives specification of the region of interest 51 on the visible image 42 in each of the aforementioned first and second embodiments, the present invention is not restricted to this. The tracking processor 32e may alternatively receive specification of the region of interest 51 on an image (the fluorescent image 41, the non-visible image 43, or the synthetic image 44) other than the visible image 42.

While the fluorescent imaging device includes the selector 32g that selects an image used for moving-body tracking from among the fluorescent image 41, the non-visible image 43, and the visible image 42 in each of the aforementioned first and second embodiments, the present invention is not restricted to this. According to the present invention, the fluorescent imaging device may not include the selector 32g. That is, the fluorescent imaging device may alternatively perform moving-body tracking based on one or more images preset from the fluorescent image 41, the non-visible image 43 and the visible image 42. In this case, one or more preset images include at least the non-visible image 43.

What is claimed is:

1. A fluorescent imaging device comprising:
   a light source unit including a first light source for radiating excitation light for a fluorescent agent administered to a subject, a second light source for radiating visible illumination light in a visible wavelength range, and a third light source for radiating non-visible light outside the visible wavelength range;
   an imager including an optical filter, the optical filter being configured to separate light in the visible wavelength range from both fluorescence outside the visible wavelength range excited by the excitation light and the non-visible light, the imager being configured to capture a fluorescent image based on the fluorescence, a visible image based on reflected light of the visible illumination light, and a non-visible image based on reflected light of the non-visible light; and
   a tracking processor that is operable to perform moving-body tracking for a region of interest that is set in an image based on at least the non-visible image.

2. The fluorescent imaging device according to claim 1, wherein the tracking processor is operable to perform the moving-body tracking for the region of interest based on the fluorescent image in addition to the non-visible image.

3. The fluorescent imaging device according to claim 1, wherein the tracking processor is operable to perform the moving-body tracking for the region of interest based on the non-visible image before administration of the fluorescent agent to the subject, and is operable to perform the moving-body tracking for the region of interest based on the non-visible image or the fluorescent image after the administration of the fluorescent agent.

4. The fluorescent imaging device according to claim 3, wherein the tracking processor is operable to use the non-visible image as an image used for the moving-body tracking at least before the administration of the fluorescent agent and is operable to switch the image used for the moving-body tracking to the fluorescent image based on a pixel value.

5. The fluorescent imaging device according to claim 1, further comprising a selector for selecting an image that is used for the moving-body tracking, the image being one of the fluorescent image, the non-visible image, and the visible image.

6. The fluorescent imaging device according to claim 5, wherein the selector is operable to switch the image used for the moving-body tracking from the fluorescent image, the visible image, or the non-visible image during the moving-body tracking by the tracking processor.

7. The fluorescent imaging device according to claim 1, further comprising an analysis processor for analyzing flow of the fluorescent agent that is to pass through the region of interest in the fluorescent image based on the result of the moving-body tracking.

8. The fluorescent imaging device according to claim 7, wherein the analysis processor is operable to generate a time intensity curve of the fluorescence generated as a result of the flow of the fluorescent agent through the region of interest in the fluorescent image.

9. The fluorescent imaging device according to claim 1, wherein the third light source is configured to radiate the non-visible light in a near-infrared wavelength range.

10. The fluorescent imaging device according to claim 1, wherein
    the third light source is configured to radiate the non-visible light in a wavelength range that overlaps with a wavelength of the fluorescence, and
    the imager includes a first imaging element for capturing the fluorescent image and the non-visible image and a second imaging element for capturing the visible image.

11. The fluorescent imaging device according to claim 1, wherein the third light source is configured to radiate the non-visible light, which substantially excludes a wavelength range of light of a fluorescent lamp.

12. The fluorescent imaging device according to claim 1, wherein the tracking processor is operable to perform the moving-body tracking of the region of interest via template matching performed between an image portion contained in an image and a template image.

13. The fluorescent imaging device according to claim 12, wherein the tracking processor is operable to perform processing of updating the template image with a captured image.

14. The fluorescent imaging device according to claim 1, wherein
    the imager is configured to capture the fluorescent image, the visible image, and the non-visible image in the same field of view, and
    the tracking processor is operable to perform the moving-body tracking of the region of interest of at least the non-visible image at the same position as that of the region of interest received on the visible image.

15. The fluorescent imaging device according to claim 1, further comprising an endoscopic device in which the light source unit and the imager are provided.

* * * * *